(12) United States Patent
Lancaster

(10) Patent No.: US 10,222,768 B2
(45) Date of Patent: Mar. 5, 2019

(54) METHOD OF AND SYSTEM FOR DETERMINATION OF MEASURED PARAMETER GRADIENTS FOR ENVIRONMENTAL SYSTEM CONTROL

(71) Applicant: EcoVent Systems, Inc., Boston, MA (US)

(72) Inventor: Nicholaus Ray Lancaster, Mineral Wells, TX (US)

(73) Assignee: EcoVent Systems Inc., Boston, MA (US)

( * ) Notice: Subject to any disclaimer, the term of this patent is extended or adjusted under 35 U.S.C. 154(b) by 382 days.

(21) Appl. No.: 15/018,250

(22) Filed: Feb. 8, 2016

(65) Prior Publication Data
US 2016/0153674 A1 Jun. 2, 2016

Related U.S. Application Data

(63) Continuation-in-part of application No. PCT/US2014/065011, filed on Nov. 11, 2014, which
(Continued)

(51) Int. Cl.
*G05B 15/02* (2006.01)
*H04Q 9/00* (2006.01)
(Continued)

(52) U.S. Cl.
CPC .............. *G05B 15/02* (2013.01); *F24F 11/30* (2018.01); *F24F 11/62* (2018.01); *H04Q 9/00* (2013.01);
(Continued)

(58) Field of Classification Search
CPC . F16K 37/0041; F16K 41/02; G01N 27/3272; G01L 1/142; G01P 15/18; F24F 2130/10
See application file for complete search history.

(56) References Cited

U.S. PATENT DOCUMENTS

| 4,538,134 A | 8/1985 | Carey |
| 4,864,269 A | 9/1989 | Priebe |

(Continued)

FOREIGN PATENT DOCUMENTS

| WO | WO-2012/013964 A1 | 2/2012 |
| WO | WO-2013/040657 A1 | 3/2013 |

OTHER PUBLICATIONS

International Search Report and Written Opinion issued by the U.S. Patent and Trademark Office as International Searching Authority for International Application No. PCT/US2014/065011 dated May 27, 2015 (17 pages).

*Primary Examiner* — Elias Desta
(74) *Attorney, Agent, or Firm* — Wilmer Cutler Pickering Hale and Dorr LLP

(57) ABSTRACT

A method of and system for determination of measured parameter gradients for environmental system control is presented. A system includes a sensor assembly with a first face opposite to and spaced apart from a second face and first and second sensors. The first sensor is adjacent to the first face and senses a first value of an environmental variable nearby. The second sensor is adjacent to the second face and senses a second value of the environmental variable nearby. The system includes a processor and a memory with instructions that cause the processor to: receive the first and second values and estimate a third value of the environmental variable at a distance spaced apart from the second face based on the first and second values. The system includes a sensor communication system for transmitting information including at least one of the first, second, and third value of the environmental variable.

16 Claims, 34 Drawing Sheets

Related U.S. Application Data is a continuation-in-part of application No. 14/264,161, filed on Apr. 29, 2014, now Pat. No. 9,723,380, and a continuation-in-part of application No. 14/264,277, filed on Apr. 29, 2014, now Pat. No. 9,854,335.

(60) Provisional application No. 62/076,911, filed on Nov. 7, 2014, provisional application No. 61/955,297, filed on Mar. 19, 2014, provisional application No. 61/902,939, filed on Nov. 12, 2013.

(51) Int. Cl.
| | | |
|---|---|---|
| *F24F 11/30* | (2018.01) | |
| *F24F 11/62* | (2018.01) | |
| *G01L 7/08* | (2006.01) | |
| *G01N 29/00* | (2006.01) | |
| *F24F 110/00* | (2018.01) | |
| *F24F 110/10* | (2018.01) | |
| *F24F 110/12* | (2018.01) | |
| *F24F 110/70* | (2018.01) | |
| *F24F 110/72* | (2018.01) | |
| *F24F 120/10* | (2018.01) | |
| *F24F 110/40* | (2018.01) | |
| *F24F 130/00* | (2018.01) | |
| *F24F 130/10* | (2018.01) | |
| *F24F 11/56* | (2018.01) | |

(52) U.S. Cl.
CPC ........... *F24F 11/56* (2018.01); *F24F 2110/00* (2018.01); *F24F 2110/10* (2018.01); *F24F 2110/12* (2018.01); *F24F 2110/40* (2018.01); *F24F 2110/70* (2018.01); *F24F 2110/72* (2018.01); *F24F 2120/10* (2018.01); *F24F 2130/00* (2018.01); *F24F 2130/10* (2018.01); *G01L 7/08* (2013.01); *G01N 29/00* (2013.01); *H04Q 2209/40* (2013.01); *Y02A 50/243* (2018.01)

(56) References Cited

U.S. PATENT DOCUMENTS

| | | | |
|---|---|---|---|
| 5,271,558 A | | 12/1993 | Hampton |
| 5,303,767 A | | 4/1994 | Riley |
| 5,364,024 A | | 11/1994 | Lin |
| 6,047,603 A | * | 4/2000 | Ohtera ................... G10K 9/122 310/322 |
| 6,648,750 B1 | | 11/2003 | Wiseman |
| 6,692,349 B1 | | 2/2004 | Brinkerhoff et al. |
| 7,168,627 B2 | | 1/2007 | Kates |
| 7,347,774 B2 | | 3/2008 | Aronstam et al. |
| 7,554,437 B2 | | 6/2009 | Axelsen |
| 7,656,664 B2 | | 2/2010 | Ye et al. |
| 7,693,809 B2 | | 4/2010 | Gray |
| 8,061,417 B2 | | 11/2011 | Gray |
| 8,244,405 B2 | | 8/2012 | Kao et al. |
| 8,289,160 B1 | | 10/2012 | Billman |
| 8,290,628 B2 | | 10/2012 | Yeo |
| 8,374,729 B2 | | 2/2013 | Chapel et al. |
| 8,467,734 B2 | | 6/2013 | Schubert |
| 8,979,622 B2 | | 3/2015 | Casey |
| 9,322,569 B2 | | 4/2016 | Scharf et al. |
| 9,618,222 B1 | | 4/2017 | Hussain et al. |
| 2004/0159713 A1 | | 8/2004 | Schmidt et al. |
| 2006/0063522 A1 | | 3/2006 | McFarland |
| 2006/0250257 A1 | * | 11/2006 | Reynolds ................ G01C 21/16 340/601 |
| 2007/0145158 A1 | | 6/2007 | Dietz et al. |
| 2007/0193361 A1 | * | 8/2007 | Coffey .................... G01L 5/243 73/780 |
| 2008/0041969 A1 | | 2/2008 | Nathan |
| 2008/0188173 A1 | | 8/2008 | Chen et al. |
| 2008/0242212 A1 | | 10/2008 | El-Galley et al. |
| 2008/0311842 A1 | | 12/2008 | Alston et al. |
| 2009/0002146 A1 | | 1/2009 | Lin |
| 2009/0065595 A1 | | 3/2009 | Kates |
| 2009/0174547 A1 | | 7/2009 | Greene et al. |
| 2010/0012737 A1 | | 1/2010 | Kates |
| 2010/0033024 A1 | | 2/2010 | Crucs |
| 2010/0083731 A1 | | 4/2010 | Hedtke |
| 2010/0163633 A1 | | 7/2010 | Barrett et al. |
| 2010/0288468 A1 | | 11/2010 | Patel et al. |
| 2011/0009045 A1 | | 1/2011 | Beckley et al. |
| 2011/0198404 A1 | | 8/2011 | Dropmann |
| 2012/0182698 A1 | | 7/2012 | Langels et al. |
| 2012/0201179 A1 | | 8/2012 | Das et al. |
| 2012/0239773 A1 | | 9/2012 | Blustein et al. |
| 2012/0275526 A1 | | 11/2012 | Hughes |
| 2013/0225944 A1 | * | 8/2013 | Greco ..................... A61B 5/04 600/301 |
| 2013/0245842 A1 | | 9/2013 | Lu et al. |
| 2013/0303554 A1 | | 11/2013 | Klein et al. |
| 2014/0005809 A1 | | 1/2014 | Frei et al. |
| 2014/0025805 A1 | | 1/2014 | Apte et al. |
| 2014/0032003 A1 | | 1/2014 | Chapel et al. |

* cited by examiner

METHOD OF AND SYSTEM FOR DETERMINATION OF MEASURED PARAMETER GRADIENTS FOR ENVIRONMENTAL SYSTEM CONTROL

CROSS-REFERENCE TO RELATED APPLICATIONS

This application is a continuation-in-part of and claims priority to International Patent Application No. PCT/US14/65011, filed Nov. 11, 2014, entitled Method of and System for Automatically Adjusting Airflow and Sensors for Use Therewith, which is related to and claims priority to U.S. Provisional Patent Application No. 62/076,911, entitled Method of and System for Automatically Adjusting Airflow and Sensors for Use Therewith, filed Nov. 7, 2014, U.S. Provisional Patent Application No. 61/955,297, entitled Method of and System for Automatically Adjusting Airflow, filed Mar. 19, 2014, U.S. Provisional Patent Application No. 61/902,939, entitled Method of and System for Automatically Adjusting Airflow, filed Nov. 12, 2013, U.S. patent application Ser. No. 14/264,277, entitled Method of and System for Automatically Adjusting Airflow, filed on Apr. 29, 2014, and U.S. patent application Ser. No. 14/264,161, entitled Method of and System for Automatically Adjusting Airflow and Sensors for Use Therewith, filed on Apr. 29, 2014; the latter two U.S. Patent Applications claim priority to U.S. Provisional Patent Application No. 61/955,297, entitled Method of and System for Automatically Adjusting Airflow, filed Mar. 19, 2014, and U.S. Provisional Patent Application No. 61/902,939, entitled Method of and System for Automatically Adjusting Airflow, filed Nov. 12, 2013; all of the above are incorporated by reference herein.

BACKGROUND OF THE INVENTION

Field of Invention

The invention generally relates to controlling one or more environmental conditions in a structure, and, more specifically, to techniques for automatically adjusting airflow from a common environmental control system into one or more spaces of a structure.

Description of Related Art

Heating, ventilation, and air conditioning (HVAC) systems are designed to maintain the health and safety of building conditions by regulating environmental variables such as temperature and humidity. Some buildings have multiple spaces or zones, the environmental conditions of which are controlled by multiple, independent, HVAC systems. For example, a building may have several floors, and each floor may have its own HVAC system.

In addition, an HVAC system can be designed to provide air flow to each space or zone (e.g., a room) within the building. In such systems, a central control unit that it part of the HVAC system can control air flow in parts of the HVAC distribution system to selectively supply air to one space or zone but not another. For example, a main air supply duct can have two branches in which each branch leads to a different room. Each of the branches can have a damper that prevents air flow through the branch. If the HVAC system detects that one room requires cooling air while the other does not, it will close the damper to the room not requiring cooling and open the damper to the room that requires cooling.

BRIEF SUMMARY OF THE INVENTION

Under one aspect of the invention, a method of and system for determination of measured parameter gradients for environmental system control are disclosed.

Under another aspect of the invention, a system includes a sensor assembly. The sensor assembly includes a first face and a second face. The second face is on the opposite side of the sensor assembly relative to the first face, and the second face is spaced apart from the first face. The sensor assembly also includes a first sensor and a second sensor. The first sensor is disposed adjacent to the first face. The first sensor is capable of sensing a first value of an environmental variable in proximity to the first face. The second sensor is disposed adjacent to the second face. The second sensor is capable of sensing a second value of the environmental variable in proximity to the second face. The system also includes a processor and a memory readable by the processor. The memory comprising instructions that when executed cause the processor to: receive the first value of the environmental variable, receive the second value of the environmental variable, and estimate a third value of the environmental variable at a distance spaced apart from the second face based on the first and second values of the environmental variable. The system further includes a sensor communication system capable of transmitting information. The information includes at least one of the first, second, and third value of the environmental variable.

In one embodiment, the sensor assembly includes the processor and the memory.

In another embodiment, the sensor assembly includes the sensor communication system.

In a further embodiment, the sensor assembly further includes an electrical plug disposed on the first face of the sensor assembly and an electrical outlet disposed on the second face of the sensor assembly. The sensor assembly is configured such that the first face is disposed adjacent to a wall surface when the electrical plug of the sensor assembly is coupled to an electrical outlet in the wall surface.

In still another embodiment, the memory further includes instructions that when executed cause the processor to receive information about a time of day and cause the processor to further base the estimate of the third value of the environmental variable on the time of day.

In yet a further embodiment, the memory further includes instructions that when executed cause the processor to further base the estimate of the third value of the environmental variable on a distance of separation between the first sensor and the second sensor.

In another embodiment, the first sensor and the second sensor are temperature sensors, and the environmental variable is temperature.

In still another embodiment, the estimate of the third value of the environmental variable at the distance spaced apart from the second face estimates the temperature of a room in which the sensor assembly is disposed.

Under another aspect of the invention, a method includes providing a sensor assembly including a first face and a second face. The second face is on the opposite side of the sensor assembly relative to the first face, and the second face is spaced apart from the first face. The sensor assembly also includes a first sensor and a second sensor. The first sensor is disposed adjacent to the first face, and the first sensor is capable of sensing a first value of an environmental variable in proximity to the first face. The second sensor is disposed adjacent to the second face, and the second sensor is capable of sensing a second value of the environmental variable in proximity to the second face. The method also includes receiving the first value of the environmental variable at a processor and receiving the second value of the environmental variable at the processor. The method further includes estimating, by the processor, a third value of the environmental variable at a distance spaced apart from the second face based on the first and second values of the environmental variable and transmitting at least one of the first, second, and third value of the environmental variable.

In another embodiment, the further includes receiving information about a time of day, and the estimating, by the processor, of the third value of the environmental variable is further based on the time of day.

In a further embodiment, the estimating, by the processor, of the third value of the environmental variable is further based on a distance of separation between the first sensor and the second sensor.

In yet another embodiment, the first sensor and the second sensor are temperature sensors, and the environmental variable is temperature.

In still a further embodiment, the estimate of the third value of the environmental variable at the distance spaced apart from the second face estimates the temperature of a room in which the sensor assembly is disposed.

In another embodiment, the sensor assembly includes the processor, and the sensor assembly further includes a transmitter capable of performing the transmitting of the at least one of the first, second, and third values of the environmental variable.

In still another embodiment, the transmitting of the at least one of the first, second, and third values of the environmental variable includes transmitting the third value.

In yet a further embodiment, the sensor assembly further includes an electrical plug disposed on the first face of the sensor assembly and an electrical outlet disposed on the second face of the sensor assembly. The sensor assembly is configured such that the first face is disposed adjacent to a wall surface when the electrical plug of the sensor assembly is coupled to an electrical outlet in the wall surface.

Any of the aspects or embodiments of the invention described above can be combined with any of the other aspects or embodiments set forth herein.

BRIEF DESCRIPTION OF THE SEVERAL VIEWS OF THE DRAWINGS

For a more complete understanding of various embodiments of the present invention, reference is now made to the following descriptions taken in connection with the accompanying drawings in which.

DETAILED DESCRIPTION OF THE PREFERRED EMBODIMENTS

Figure 1:
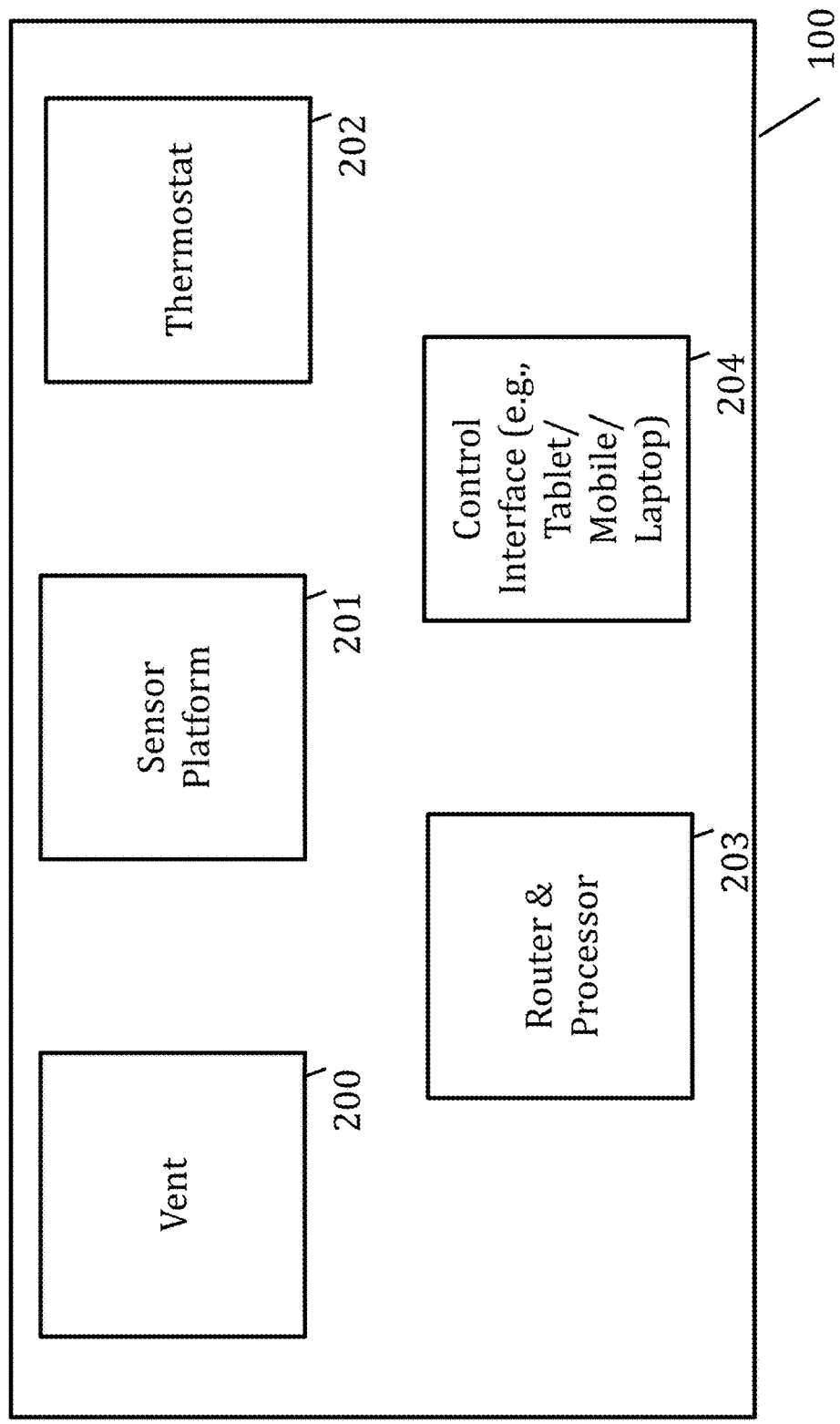
FIG. 1 illustrates an overview of a system for automatically adjusting airflow in a building according to an embodiment of the invention.

A system (100) described in this document is a novel approach to optimizing the airflow in a building (e.g., a home) based on user set goals for savings, comfort or both. In this implementation, the system is comprised of five major components as seen in FIG. 1. In one implementation there is a wireless Router & Processor that deploys a pre-configured wireless network (203) which communicates with the vents (200), Sensor Platforms (201), Thermostat(s) (202) and the Control Interface (204).

Figure 2:
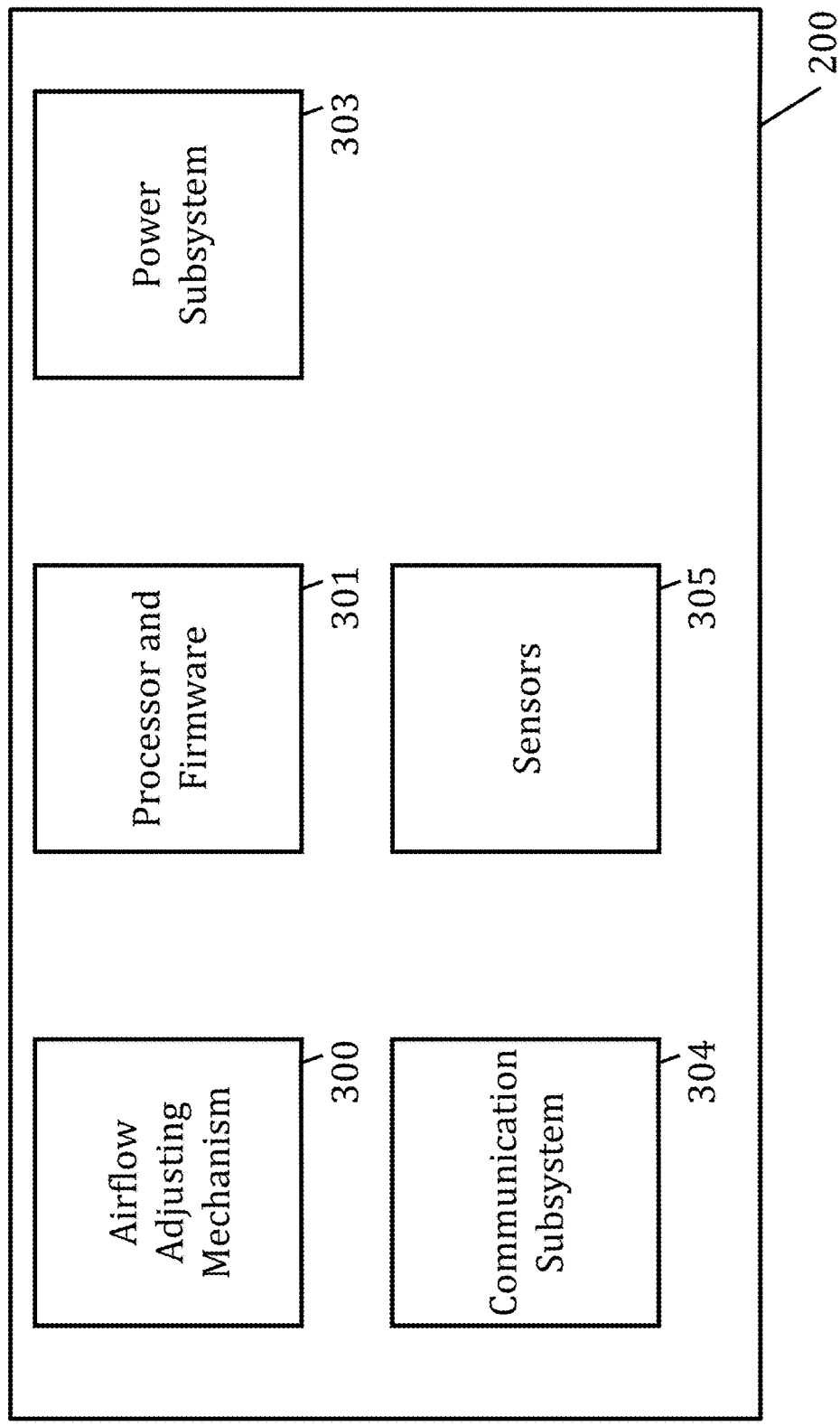
FIG. 2 illustrates an overview of a vent for automatically adjusting airflow to a space according to an embodiment of the invention.

In one implementation of the system, all of the vents in a home are replaced with new wirelessly controlled actuating vents (also called "vents" or controlled supply registers herein). In other words, the traditional covering (or faceplate) of the terminus of a portion of the duct work of a forced-air heating or cooling system is replaced. In an illustrative example, the terminus of the duct work is the location at which the duct stops flush with the wall or ceiling of a room. In another embodiment, only a few of these vents would need to be replaced. These vents allow the system to control the airflow within the existing ductwork, without damaging the HVAC system due to lack of airflow, within a home. Embodiments of such vents are shown in FIG. 2. In another embodiment no new vents are installed, but the system operates using impulses from the sensors alone. In this type of system, the HVAC is turned on/off based on temperatures in any room in the home—allowing much more control. For example, a user can instruct the system to maintain a bedroom at a desired setpoint. The system would cycle on and off to maintain the desired setpoint in the bedroom without regard for how the other rooms are affected. In another example, the system can be configured with more complex instructions, such as attempt to maintain a first room at a first setpoint but only if a second setpoint set for another room is not exceeded. In all cases the conditions inside of the ducts are measured and taken into account when controlling the vents. These are examples only, and other configurations are within the scope of the invention. In addition, while implementations of the invention are described as being used with HVAC systems, it is understood that systems that only heat, only cool, or only supply forced air are within the scope of the invention.

In one embodiment, the added vent closing device may be added into main return ducts. In another embodiment, an airflow control device may be added to a fresh air intake. With these additions the system can control outdoor air intake to improve energy efficiency, or meet occupancy fresh air demands if paired with $CO_2$ sensors. In one embodiment, this system may be operated as an HVAC economizer, or include operations that resemble an economizer. The system can thus add outdoor air when temperature or humidity conditions are favorable to driving the system temperatures in the right direction (heating or cooling, dehumidification or humidification). This will allow for "free" heating or cooling, as the system need not operate the heat pump, furnace, AC unit, or other cooling device to control the temperature, dramatically reducing energy consumption.

Figure 3:
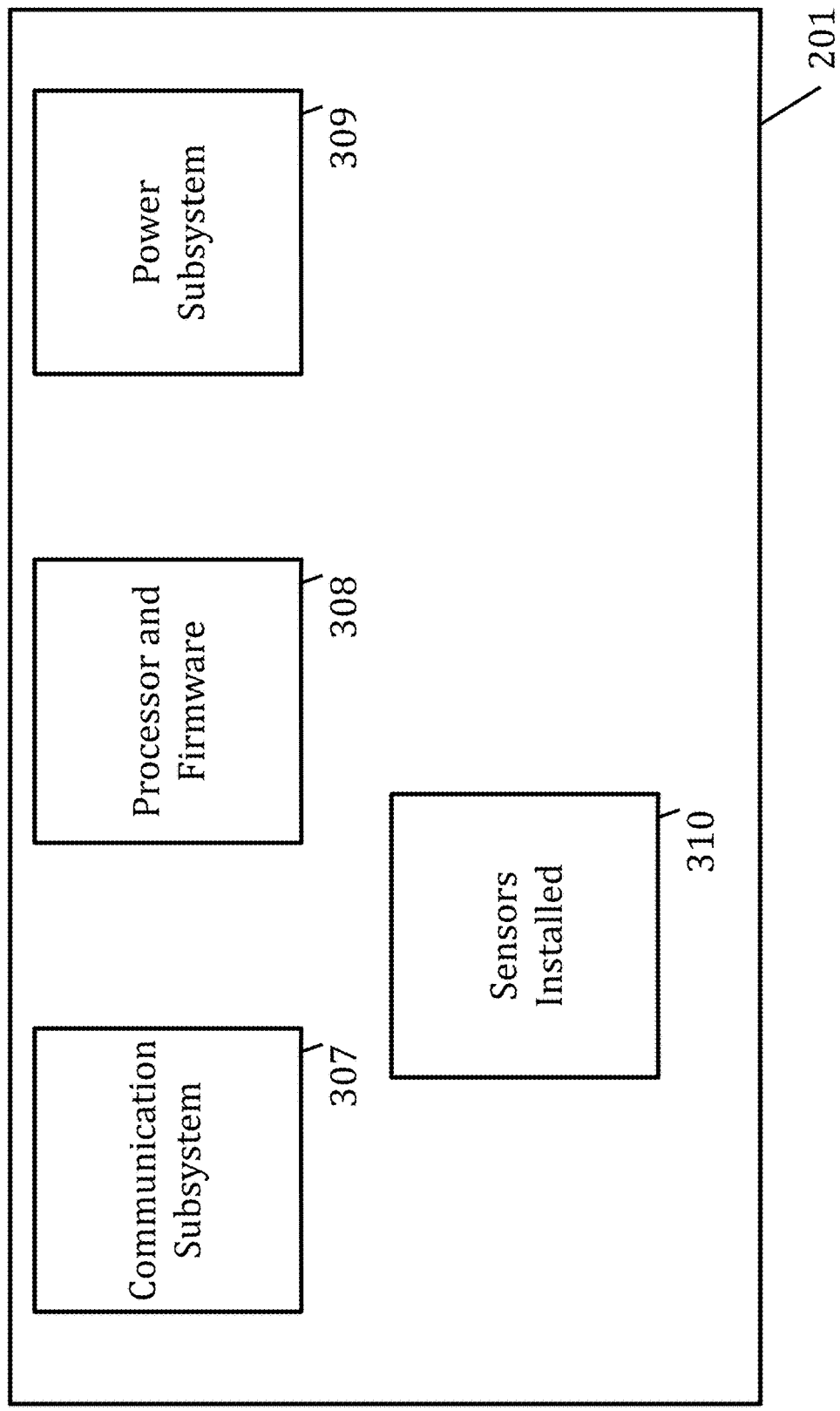
FIG. 3 illustrates an overview of a sensor platform for detecting a condition in a space according to an embodiment of the invention.

In one embodiment, the Sensor Platforms (201), as seen in FIG. 3, provide the Router & Processor (203) with real time data on the temperature, humidity, air pressure, and motion in the rooms within the home or building. The sensor platforms provide feedback to the Router & Processor which in turn controls the vents.

Embodiments of this system can vary in that the configuration of the vents (in quantity, integrated sensors, and opening and closing mechanisms), the sensor platforms (in both types of sensors installed (i.e. pressure sensors, multiple temperature sensors), as well as location and quantity), and the network protocol can change or adapt as long as there is a method for the system to receive feedback regarding the state of the home or building within which it is installed. This means, in various embodiments, only a few sensor platforms may be necessary if the system can determine the states of the whole home or building through correlation. In yet another embodiment, only one sensor may be installed, which is moved from room to room over a period of time, to develop an understanding of the home. In yet another embodiment, no sensors are deployed, and the system would gather feedback by querying the user.

In one embodiment, the system is added to a fixed volume air conditioning system. In another embodiment, the system is added to an existing variable air volume system for added control or to supplement problem areas. In another embodiment, the system is added to an active chilled beam system. In yet another embodiment, the system is added to a DOAS (dedicated outdoor air system). In other embodiments, the system may be added to other HVAC or other fluid providing systems.

Figure 6:
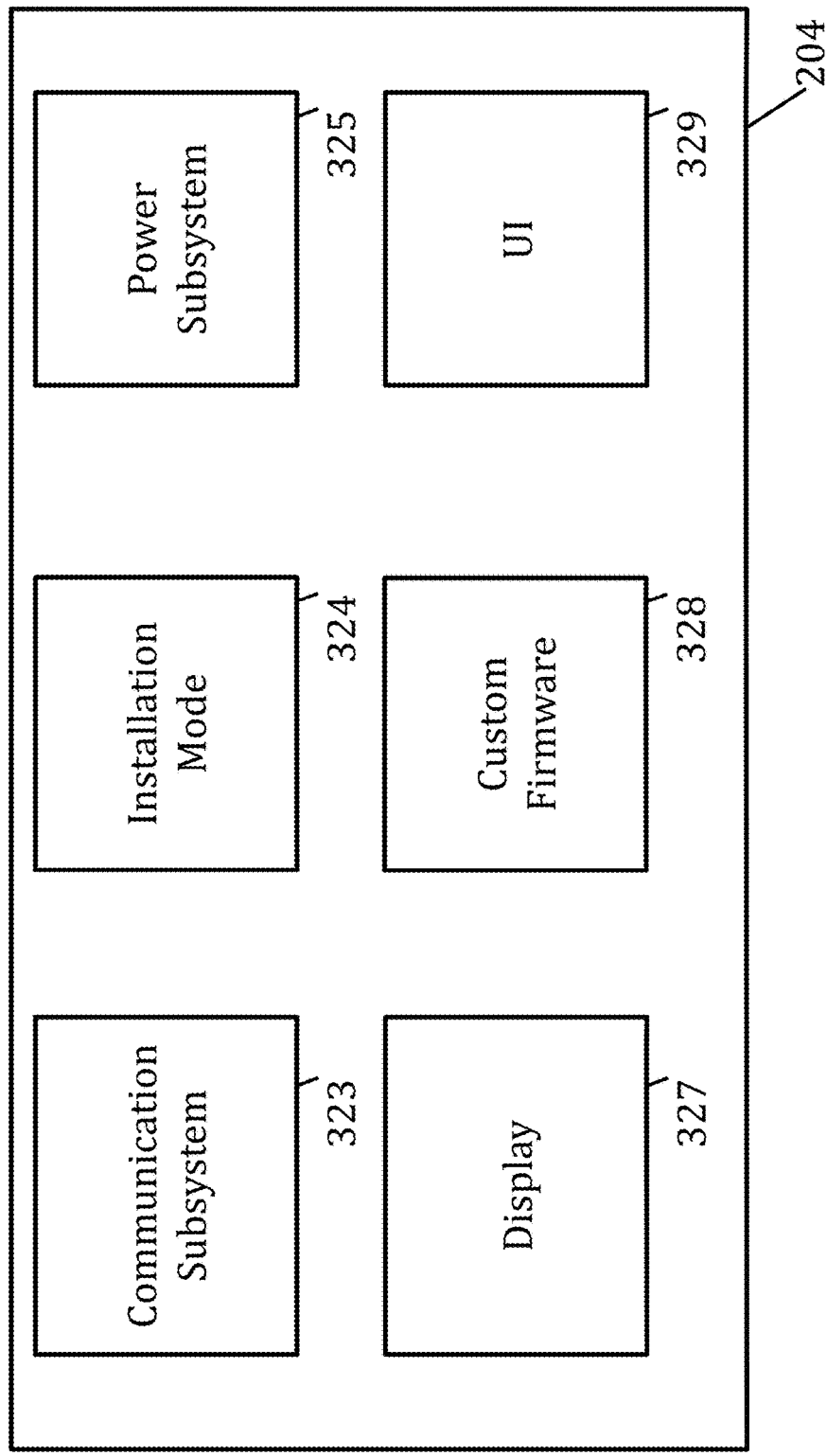
FIG. 6 illustrates an overview of a control interface according to an embodiment of the invention.

To control the system, in one embodiment the user uses the Control Interface (204), as seen in FIG. 6, to instruct the Router & Processor on the user's preferences for mode and/or temperatures for each room. Using the user's preferences (e.g., environmental variable set points), and feedback from the sensors, the Router & Processor adjusts the vents throughout the home in response to changing conditions to optimize the airflow and help the home reach equilibrium. More details and embodiments for the control interface are described later in this report.

In one embodiment, the system operates based on anticipated and/or current occupancy. The system may use occupancy-use patterns for each room or combinations of rooms to determine what hours of the day and days of the week to operate. In one embodiment, the system uses occupancy sensors, which may include infrared, acoustic (passive or active ultrasonic sensors), microwave detector sensors, or other sensors. In another embodiment, the system may detect a device on a person, such as a smartphone, tablet, laptop, or other wifi/Bluetooth/electromagnetic wave emitting device to detect occupancy. In one embodiment, the system may interface with existing or new lighting systems that employ occupancy sensors, using the same sensors for both. In controlling the zones and adapting, the system may employ adaptive control, neural networks, fuzzy logic, thermodynamic modeling of HVAC zones, fan power energy consumption modeling, minimum outdoor air, room use type, predictive heating demand control, dynamic occupancy patterns, or other control methods. In another embodiment, the system operates based on fixed schedule. In yet another, the system operates using preferences set by the user. In yet another, the system allows individual zoning of each room, allowing the user to set the conditions of each room independently.

In one embodiment, the system uses pressure as an input. In another embodiment, the vents use pressure and temperature as inputs. By measuring the pressure within the ducts, or calculating it based on other measurements, the system can prevent creating a pressure environment that impacts the health of the existing HVAC system, or efficiency. By using both pressure and temperature a better estimate of system health is obtained. In one embodiment, the vent (as shown in FIG. 2) has pressure sensors on the device. In another, pressure sensors are placed within or affixed to the duct and communicate to the system. In one embodiment, pressure may be measured on the sensor platform (as seen in FIG. 3), then calculations can be applied to understand the pressure on the system. In another, the pressure measurement is used to calculate volumetric airflow through the vent. In another embodiment pressure is measured on each sensor platform. By using pressure and temperature measurements at all, or even a subset of, sensors and vent locations the local temperature gradient can be deduced. This calculation allows comfort at any height in the building to be calculated and better controlled. When determining a temperature or any other gradient for an environmental variable, the information about the environmental variables can be collected by a sensor information aggregator. The aggregator can use manual locations for the sensors provided by the user or the system can determine the positions of the sensors relative to each other using wireless communication signal strength between the sensors and the location of the aggregator. The aggregator can reside in any of the components of the system described herein, and it performed the determination of the gradient value based on the information supplied by the various sensors.

In one embodiment the Router & Processor (FIG. 5) controls the existing HVAC unit within the home through the thermostat (202), which receives wireless instruction from the processor and thus actuates the HVAC system. In yet another, the system may instruct the user to turn on and off their system. In yet another, the router and processor may communicate directly to the HVAC unit through a wireless interface built into the HVAC, or added on. The concept here is that the Router & Processor, using feedback from the sensor platforms, vents, and a smart learning control algorithm that optimizes the use of the HVAC system for any situation. The algorithm uses machine learning techniques in combination with data collected from the vents, sensors, and user inputs to learn the characteristics of the home including heat loads, air leakage, humidity load, forced air pressure characteristics, and others. Once the algorithm learns the characteristics of the home, the use of the HVAC system can be optimized according to a blend of comfort and economy according to user preferences. For example, with certain HVAC systems, the algorithm can operate the fan and compressor separately to address issues such as stack effect in multi-story homes by turning the compressor off while leaving the fan running. The user can also be alerted to sudden changes in system characteristics that may indicate an anomaly that warrants attention. In one embodiment the algorithm learns the home characteristics through normal use. In another the algorithm exercises the entire home HVAC and system components in order to learn more quickly and completely the home characteristics.

In an illustrative implementation, the temperature of air returning to an HVAC system is monitored using sensor devices (500) present in the rooms of a building. Meanwhile, air exiting the HVAC system is monitored using sensors present on the vents (200) of the rooms. This information provides a temperature change achieved by the HVAC system. Using known techniques, the system, e.g., by the Router & Processor (203), can estimate an efficiency of the HVAC system. This efficiency can be tracked over a period of time to establish a baseline efficiency. From time-to-time, the current operating efficiency can be compared against the baseline to determine if the efficiency has fallen passed a threshold. Likewise, the operating efficiency data can be monitored to detect a downward trend.

When the system detects a downward efficiency trend or that the current operating efficiency has fallen below a threshold, the system informs the system's user, building owner, maintenance contact, or the like. Such a notification can take place via a message presented on the Control Interface (204), via an electronic mail message, or other known techniques.

Optionally, the system, e.g., by the Router & Processor (203), can take into account other sensor measurements, such as pressure, humidity, etc., when performing the efficiency estimate calculations. Similarly, the system can obtain current weather information from a weather information source via a network connection. For example, the system can take outside ambient temperature, wind, hours of sun, cloud cover, and/or other environmental attributes into account in the efficiency calculations. This additional information can be correlated with the HVAC performance information and stored for analysis. For example, the system can gather information on the HVAC system's performance and efficiency during summer air conditioning cycles. The system, e.g., by the Router & Processor (203), compares the temperature difference between the HVAC system input and output for days that have similar temperature trends, hours of sun, and/or amounts of cloud cover. If the system determines that the air output from the HVAC system during air conditioning cycles is becoming warmer over time despite the environmental conditions being comparable, the system will alert the designated individual that the HVAC efficiency appears to be decreasing.

The system can also track and compare other information to detect decreasing efficiency and/or performance trends, such as HVAC system run hours, total system airflow output, static pressure measurements at points in the HVAC system, temperature trends in the HVAC system, and other known performance measures. Similarly, the system can monitor for HVAC faults or problematic conditions, such as temperature, pressure, and/or humidity extremes. Further still, the system can receive information from sensors present in the HVAC system as a whole, e.g., fan motor temperature sensors, electric consumption meters for individual HVAC system components, gas consumption meters, and coolant line temperature sensors. Likewise, the system can alert the designated individual if the system calls for operation of the HVAC system but does not detect airflow through the vents or detects a lack of air temperature change passing through the HVAC system despite expected heating or cooling.

The Vent, as shown in FIG. 2, includes an Airflow Adjusting Mechanism (300), a processor with firmware (301), a power subsystem (303), a communication subsystem (304), and sensors (305). In one embodiment, the vent receives wireless instructions from the Router & Processor (203) via the communication subsystem (304). In another, the vent may receive wireless instructions directly from the sensor platforms. In another, the vent may receive wireless instructions directly from the Control Interface.

The Vents in the system are the component of the system that impacts airflow within the house in a real time fashion. The vents open and close using an airflow adjusting mechanism (300) that control the amount of air allowed through the vent when the system is running. The sensors on the Vent can optionally include an air flow measurement device.

Figure 13:
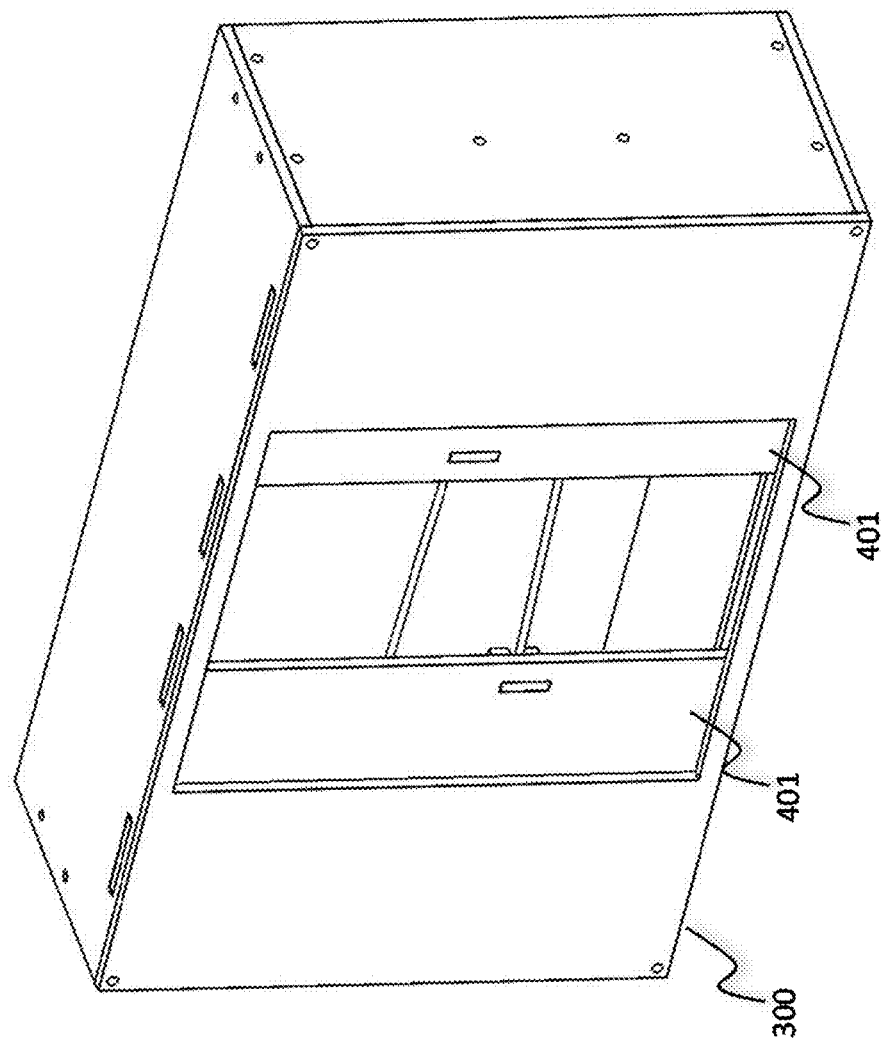
FIG. 13 illustrates an exterior perspective view of a vent according to an embodiment of the invention.
Figure 14:
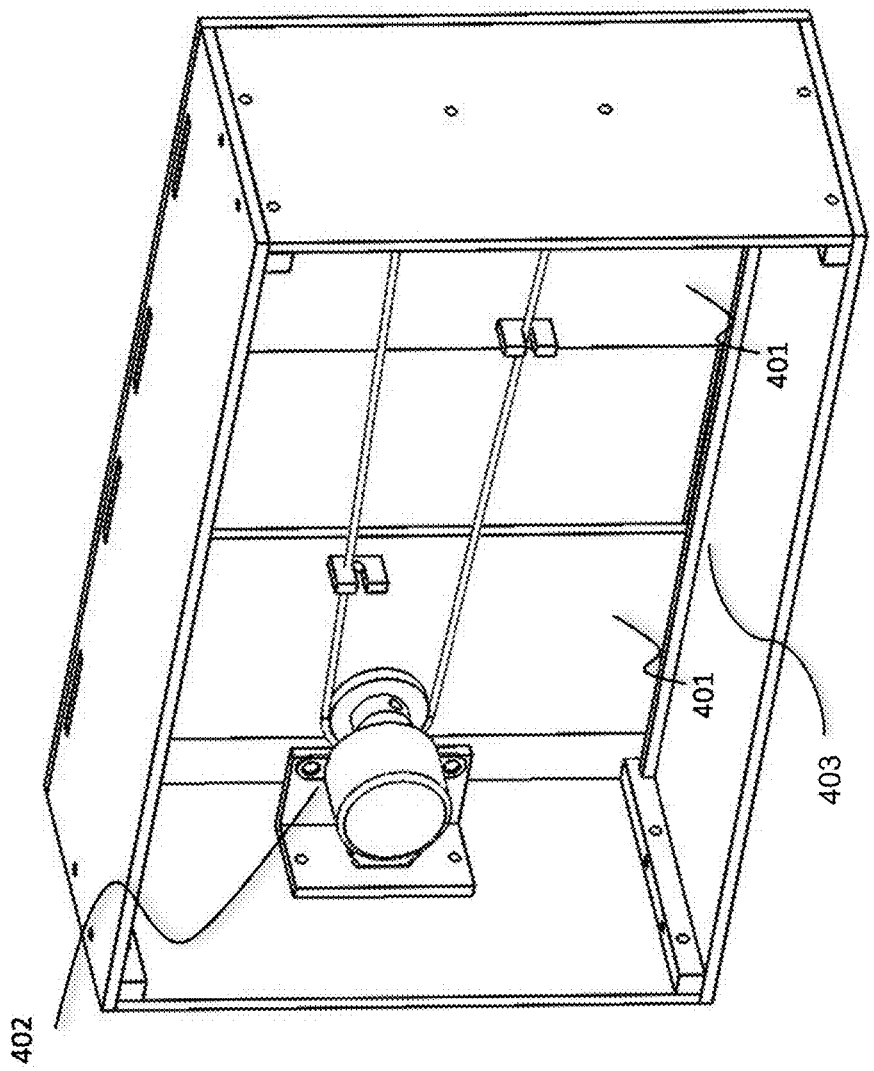
FIG. 14 illustrates an interior perspective view of a vent according to an embodiment of the invention.

There are a few components in certain embodiments of the vent (pictured in FIGS. 13,14). The first being the airflow adjusting mechanism themselves (300). This airflow adjusting mechanism is comprised of a mechanism that constricts the air (401), and a mechanism to control the constrictor (402). With regard to the constricting mechanism (401), these are the devices that constrict the air. They are controlled by a movement mechanism that serves to adjust the constriction level. The movement mechanism (402) operates the constricting mechanism in response to an instruction received from an outside controller, such as the processor and firmware (301).

With regard to the air constricting mechanism (401), in one embodiment, the louvers are horizontally mounted. In another, they are vertically mounted. Yet in another embodiment, these louvers are a shutter mechanism, similar to that of a curtain that is mounted horizontally or vertically. In certain implementations, two of the curtains' opposing edges ride in tracks. For example, as shown in FIG. 14, the lower edges of left and right constrictor portions (401) ride in a lower track (403). Similarly, the top edges of the constrictor portions (401) ride in an upper track (not shown). The vent opening forms in the middle of the vent as the constrictor curtains part. In some embodiments, the curtain is a relatively soft membrane with vertical ribs that provide rigidity. The ribs ride in the track along with the edges of the curtain. The curtain and/or rib material, as well as the tracks, can be made using relatively low friction materials, (e.g., nylon, polytetrafluoroethylene (PTFE), polyoxymethylene, PTFE infused polyoxymethylene, ultrahigh-molecular-weight polyethylene, or the like) in order to preserve battery life by reducing the power required to actuate the constrictors (401).

Yet in another embodiment, the mechanism is an iris, similar to that of a camera aperture. In still a further embodiment, this mechanism is a parachute configuration, where a semi rigid membrane is extended to catch the air. A novel concept here is to constrict the air in a manner best suited for the needs of the system. This includes balancing reliability with cost, motion with battery life, and constricting the air in a manner to minimize audible noise and other undesired side effects. Moreover, adjustments in airflow can take into account future weather forecasts when determining what is needed to maintain a user's desired environmental variable set point. In one embodiment, the air constricting mechanism replaces the existing exterior duct grill. In another embodiment, the air constricting mechanisms is mounted in the interior of the duct. Interior mounting may use springs with significant normal force, screws, adhesives, or other methods.

In one embodiment, adjustable size louvers will be added to fit different duct sizes, for either interior or exterior grills. In one embodiment, duct louvers telescope, to adjust to larger sizes. Space between louvers may vary as well, with hinges, springs, or other methods to adjust the spacing. In one embodiment, the system employs a fabric which constricts to block flow. In another embodiment, the system may include multiple arms or springs to allow for installing at a slanted angle relative to the duct, allowing for application to multiple different heights.

Figure 34:
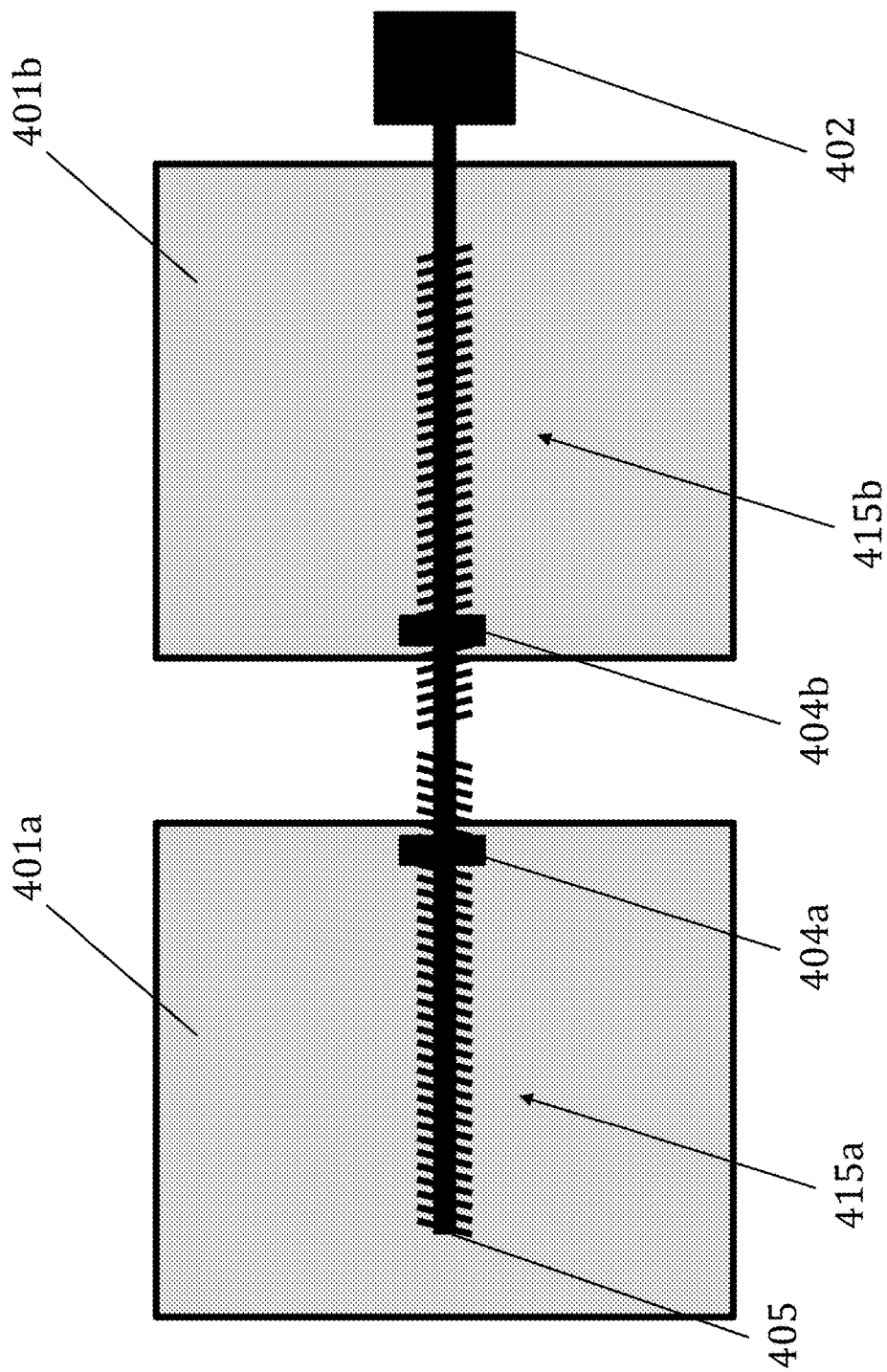
FIG. 34 illustrates an arrangement for actuating a pair of constrictors.

With regard to the mechanism that controls the constrictors (402), in one embodiment, a motor is used. In another, a stepper motor is used. In further embodiments, a travelling-nut linear actuator is paired with a motor or stepping motor, in which one or more nuts are coupled to the movable constrictors (402). FIG. 34 illustrates an implementation of such an embodiment. FIG. 34 shows a pair of constrictors (401a, 401b), each of which is actuated by a travelling nut (404a, 404b) moving along a left- and right-handed screw (405). One travelling nut (404a) is coupled to the left portion of the constrictor pair (401a), and a second travelling but (404b) is coupled to the right portion of the constrictor pair (401b). The left portion (415a) of the screw (405) is left-hand threaded, while the right portion (415b) is right-hand threaded. As the mechanism that controls the constrictors (402), e.g., a stepper motor, rotates the screw (405) in one direction, the pair of constrictors (401a, 401b) is brought together. Conversely, as the stepper motor (402) rotates in the opposite direction, the pair of constrictors (401a, 401b) is parted. Such an implementation offers the advantages of having only three moving parts for imparting movement to the constrictors. This low number of moving parts enables relatively quiet and reduced maintenance operation. It also offers a relatively low cost solution because all parts other than the stepper motor can be injection molded. This particular design also allows the mechanical advantage to be changed without changing the outer dimensions of the drive system.

In yet another, a solenoid is used. In yet another embodiment, memory wire, or metal that changes shape due to an electrical impulse is used. In yet another embodiment, electromagnets are used. In another embodiment, a material that changes shape at different temperatures due to thermal expansion is used. In even another embodiment, the air coming from the duct is used to adjust the constrictors.

The Airflow adjusting mechanism (300), as seen in FIGS. 2 and 13, is controlled using custom firmware loaded on a processor (301). This firmware has algorithms to accept commands from the main Router and Processor (203) or other outside controller to control the vent itself. It has algorithms to open and close vents, send sensor information and state information back to the router and processor, and intelligence to minimize power use of the vent itself. It also has algorithms to process the information from the onboard sensors on the vent (305).

The processor and firmware receives instructions from the router and processor (203) via the communication subsystems (304). The communication sub system receives signals wirelessly through Wi-Fi (802.11). In other embodiments, the system receives signals via an analog RF signal, ZigBee, 802.15, Z-Wave, Bluetooth, infrared, other types of electromagnetic waves, or another wireless method. In another embodiment, the system communicates via electrical wires, a wired configuration. In other embodiments, the system and subsystems may communicate in any combination of the above methods.

It is noted that in one embodiment, the communication subsystem (304) and the Processor and Firmware (301) are integrated into a single device.

Figure 5:
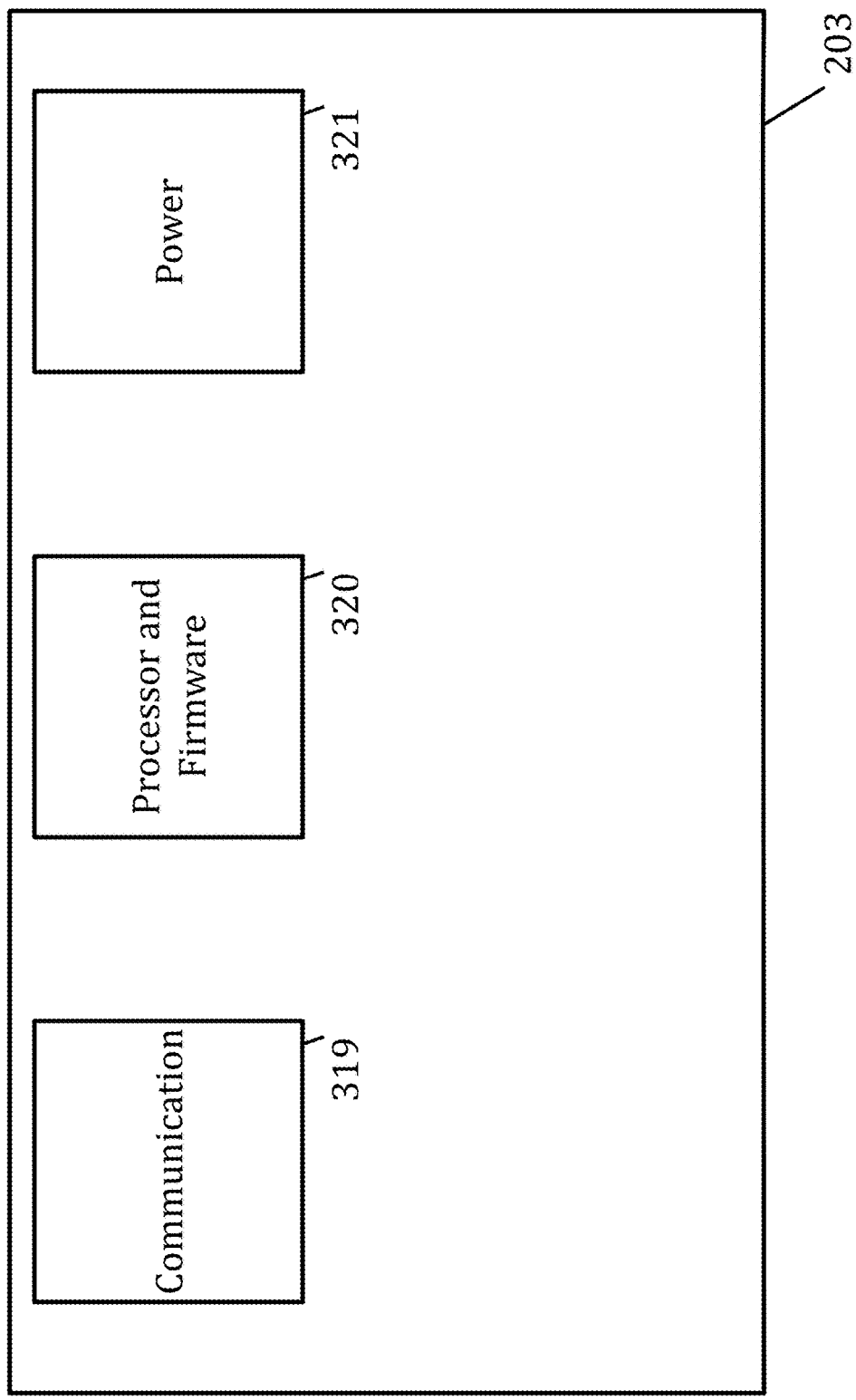
FIG. 5 illustrates an overview of a router and processor according to an embodiment of the invention.

In one embodiment the vent includes sensors (305) such as pressure and temperature sensors (408), as shown in FIG. 5, on the vent to monitor real time pressure in all ducts to avoid placing the HVAC system in a stressful or damaging environment. In other embodiments, other sensors are included, such as sound, air speed, temperature, humidity, $CO_2$ levels, occupancy, and other sensors as well. In yet another embodiment, sensors may be removed entirely. In one embodiment, the sensors on the vent's primary purpose is to understand the airflow characteristics (such as velocity, pressure, temperature, humidity) being presented to the HVAC system for the purpose of preventing damage to the system while modifying those airflow characteristics. As stated above, in addition to determining environmental characteristics inside of the duct in which it is disposed, all or any subset of the sensors on the vent are used to determine environmental characteristics of the room in which the vent is disposed. In some embodiments, readings from sensors present in the vent (200) are only taken to be representative of the room when no air is flowing through the vent.

Figure 15:
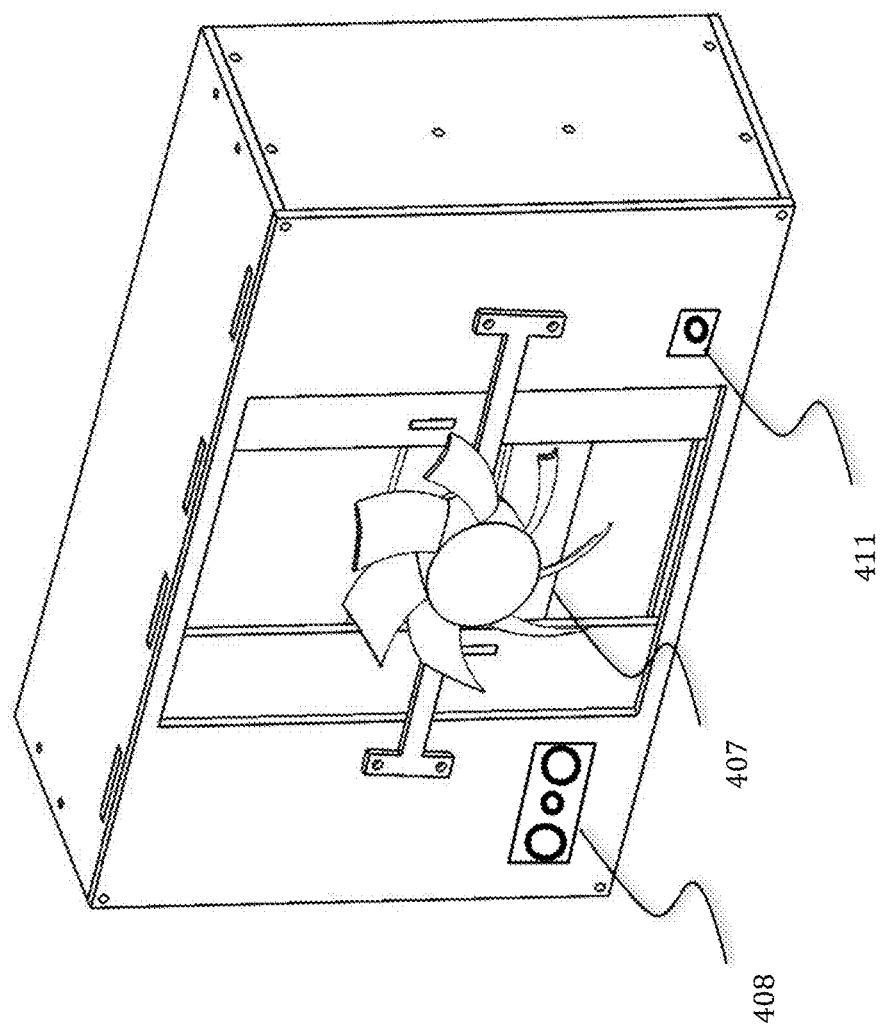
FIG. 15 illustrates an exterior perspective view of a vent according to an embodiment of the invention.
Figure 16:
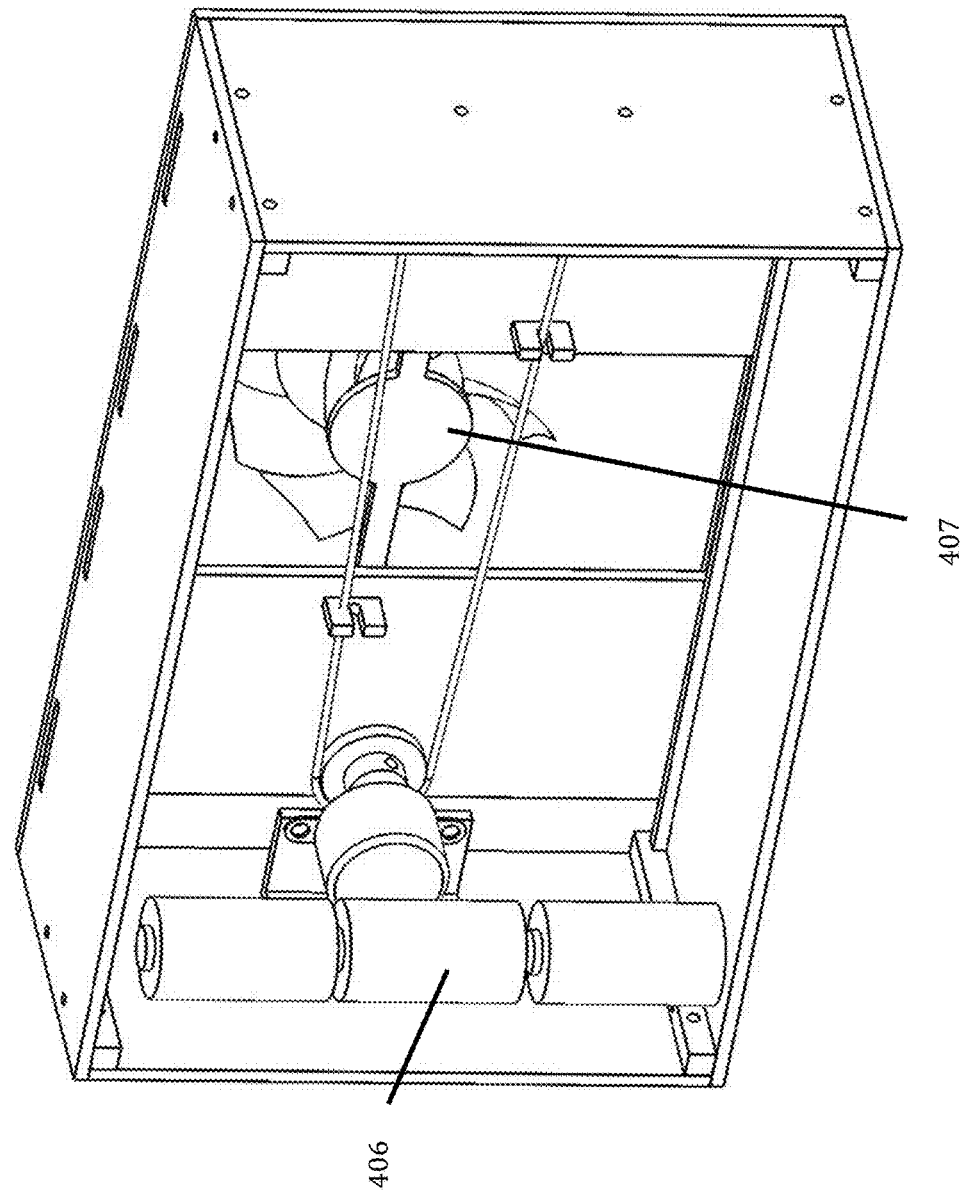
FIG. 16 illustrates an interior perspective view of a vent according to an embodiment of the invention.

In one embodiment, the vent is wireless. As such, they include a power source on the vent itself. The power subsystem (303), in one embodiment includes a battery (406). To maximize battery life, the vent may also include power generation (407) on board as shown in FIGS. 15 and 16, for use with a rechargeable battery. This power is generated using the air within the vent itself through a turbine. In another embodiment, the power is generated using vibration within the vent. In yet another embodiment, power is generated using solar panels. In another embodiment power is generated via a thermo-electric device such as a Peltier generator. In another embodiment, power is provided by a capacitor. In another embodiment, a means of mechanical energy storage such as a spring may be used. In yet another embodiment, a piezoelectric device may be used, which may capture vibrations or be paired with a part moved by the airflow. This part may use a flexible horizontal plate that oscillates in the airflow, an unstable small "wing" that uses lift to oscillate, or other devices. In yet another embodiment, power is provided to the vents via a power source such as a local outlet, or the central breaker. In still a further embodiment, the system uses inputs and historical information in order to minimize movement of the air constricting mechanism and communication times, thereby maximizing battery lifetime. This algorithm may include provisions for battery self-discharge curves, changing torque requirements with device age, estimated run and off times of the HVAC system, user habits, and weather conditions.

In one embodiment the system includes active noise cancellation technology (411) on the vents. In this embodiment the vents reduce noise levels due to airflow and ducting by actively cancelling the noise before it exits the vent. In such an implementation, a noise cancellation module samples the noise arriving at the vent from within the ducting with one or more microphones, determines the appropriate sound waveform to reduce the noise level, and produces the waveform using one or more speakers within the vent.

In one implementation, vents may use seals or gaskets on the outside to ensure a tighter seal once the vent is installed to maximize efficiency and comfort. In another, vents may clamp against the duct to ensure a tight seal. In another embodiment, duct insulation may act as a barrier to air leakage.

In another embodiment, the system acts to encourage airflow instead of restricting it, employing a fan or other device to provide additional driving force for the air.

In one implementation, the processor and firmware (301) of a vent (200) determines the volume of air passing through the vent based on the position of the constrictors (401) and a pressure drop across the vent. The position of the constrictors is provided by information from the mechanism that controls the constrictors (402), such as a stepper motor. The pressure drop across the vent is determined by a reading taken from a pressure sensor (305) inside in the vent and the ambient pressure outside the vent. The ambient pressure can be taken from a second pressure sensor on the outside of the vent, from a sensor device (500) present in the same or a different room as the vent, from a current barometric pressure reading provided by a weather information source via a network connection, or based on an assumed value.

In certain embodiments, a simple lookup table is provided in the processor and firmware (301) of the vent (200) that relates the constrictor controller (402) position and pressure drop across the vent to a volumetric flow rate. The constrictor controller position can be determined using the techniques discussed in more detail below. The flow rates can be derived from empirical testing or from fluid flow calculations and/or simulations. In other embodiments, the processor and firmware (301) of the vent (200) are configured with information that relates the constrictor controller (402) position with the size of the opening created by the constrictors. The vent then calculates the volumetric flow rate using the vent opening size and pressure drop.

In still further embodiments, a vent (200) can be "self-calibrating". In such an implementation, the processor and firmware (301) of a vent (200) is provided with the maximum vent opening size and the relationship between the positional changes of the constrictor controller (402) and the vent opening. For example, for a constrictor (401) that is a two part curtain mounted horizontally (as shown in the embodiment in FIGS. 13 and 14), there is a linear relationship between the area of the opening and the relative position of the constrictors. In other words, if the constrictors are halfway open, the size of the vent opening will be half of the maximum vent opening size. During an initialization step, the processor and firmware (301) of the vent (200) causes the stepper motor (402) to move the constrictors (401) from completely open to completely closed and counts the steps in-between the opened and closed positions. The processor and firmware (301) of the vent can detect the opened and closed stop positions through the use of a position sensor or based on back electro-motive force from the stepper motor, using techniques known in the art. Optionally, the flow rate determinations can take into account the temperature of the flowing air using a temperature sensor present in the vent (200).

In certain embodiments, the processor and firmware (301) of the vent (200) collects all necessary information to make the flow rate determination and transmits the information to an external processor for flow rate determination. For example, the Router & Processor can serve as the external processor.

Figure 17:
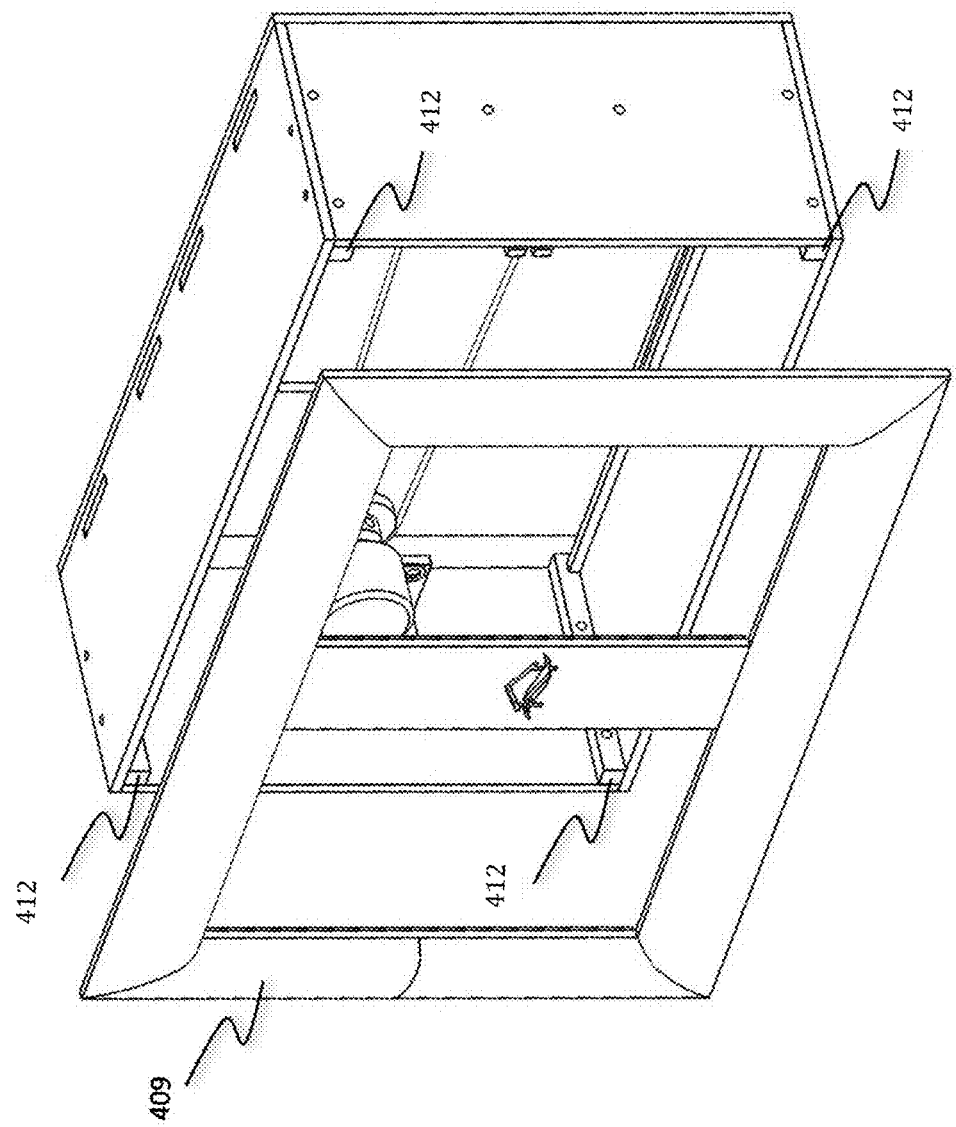
FIG. 17 illustrates an exterior perspective view of a vent with a faceplate according to an embodiment of the invention.

FIG. 17 presents a front plate (409) that can be installed and removed without tools. In one embodiment, the plate is attached with magnets (412). In another, a hook and loop attachment is used; further still, a slide mechanism is used in another.

Figure 18:
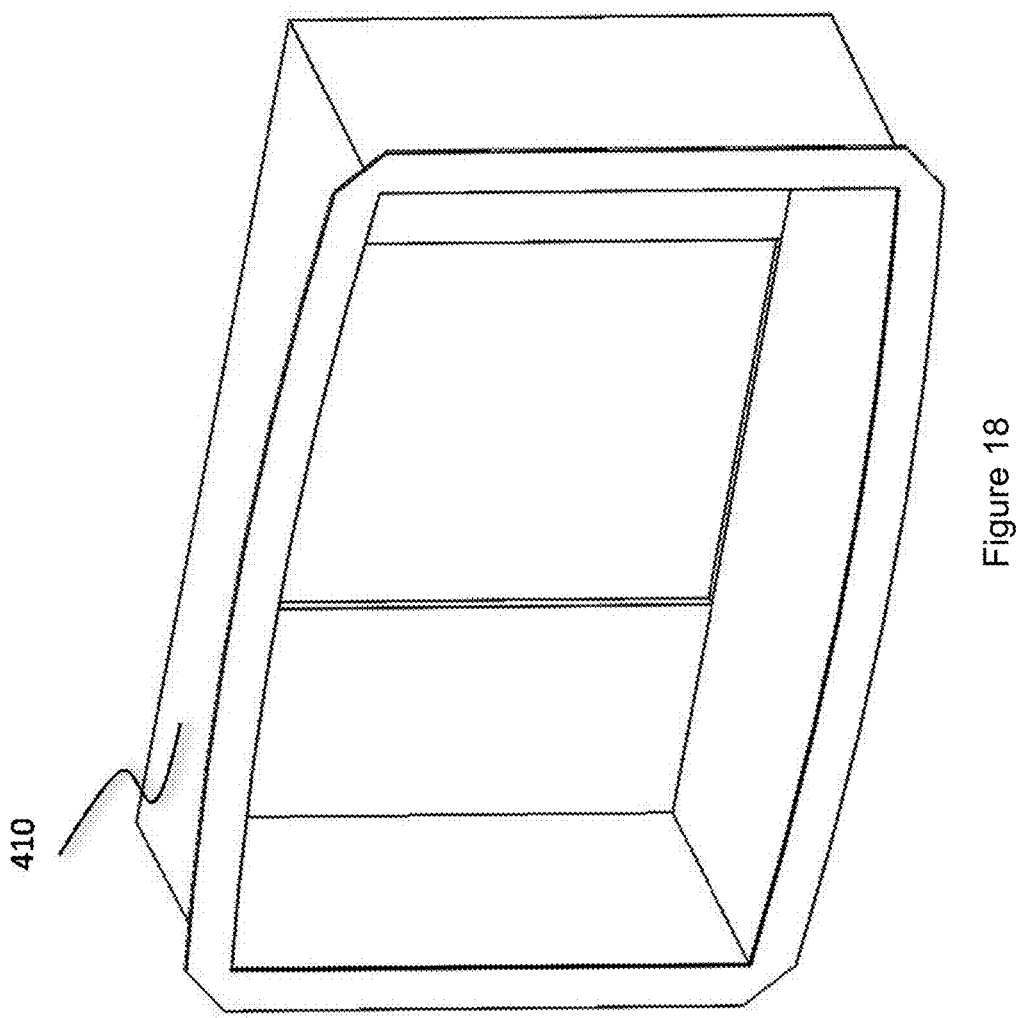
FIG. 18 illustrates a perspective view of a vent fitting according to an embodiment of the invention.
Figure 19:
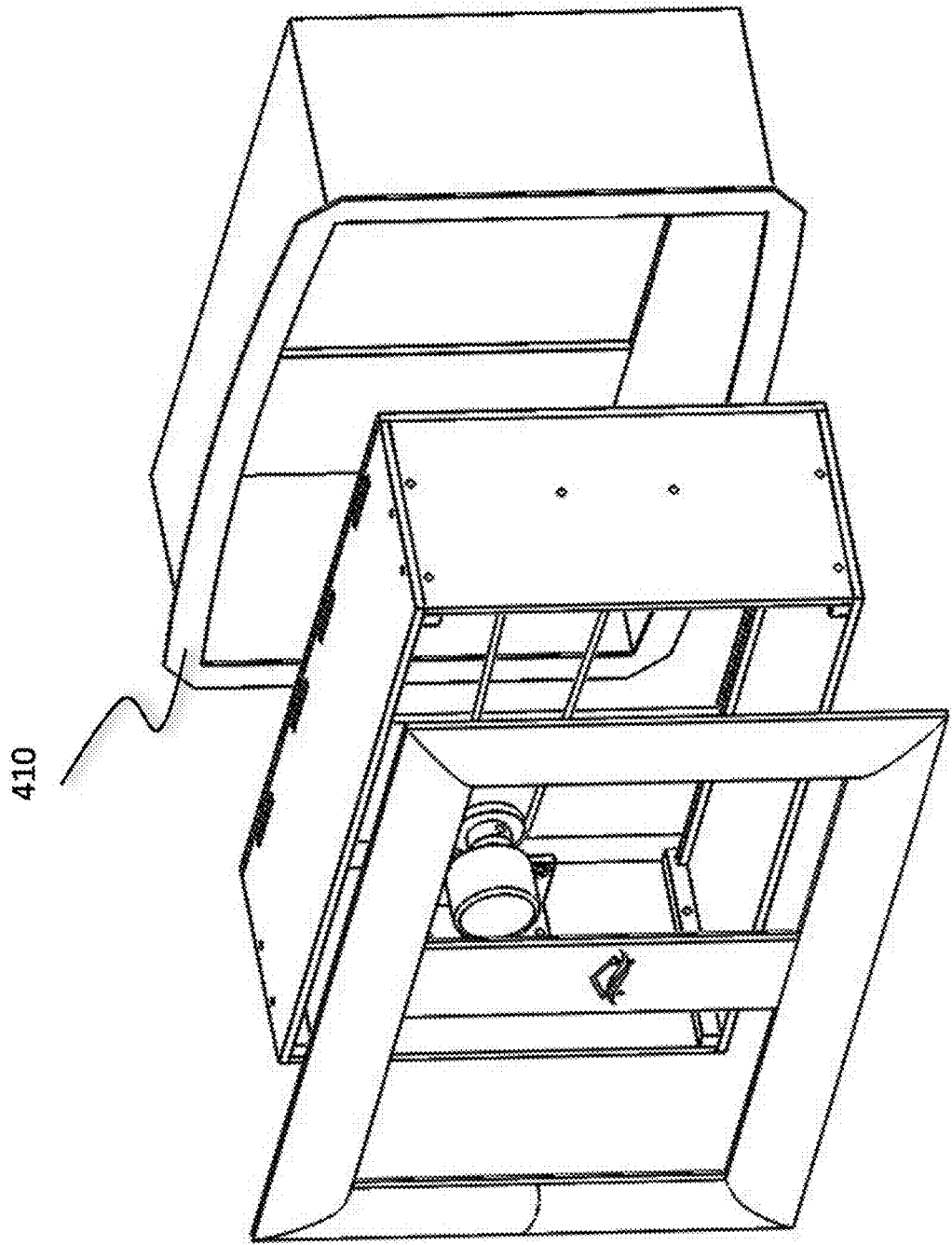
FIG. 19 illustrates an exploded perspective view of a faceplate, vent, and vent fitting according to an embodiment of the invention.

In one embodiment the vent installs in the home without the use of tools. In one embodiment this is accomplished by a warped shape (410) in the vent that creates a friction fit as shown in FIGS. 18 and 19. Specifically, the top and bottom of shape (410) are bowed slightly outward. In another a lever mechanism engages the wall. In another, wedges may be inserted by hand between the vent and the duct.

The faceplates of the vents are designed to diffuse air in a more efficient and quieter manner. These faceplates provide the same amount of diffusion, while presenting a lower pressure load on the existing HVAC system—meaning the vents themselves are more efficient than existing solutions. By lowering the "all open" pressure, the vent allows more potential to add pressure to the system without reaching a damaging state. In other words, such vents have a greater range of back-pressure available.

In one embodiment of the system, the sensor platform (201) is employed to provide feedback to the Router & Processor.

In one implementation, the sensor platform, as seen in FIG. 3, uses temperature, motion, and humidity sensors (310) to detect characteristics of the environment and send that information through the Processor and Firmware (308) via the communication subsystem (307). In another implementation, the sensor platform senses ambient pressure. In this embodiment the sensors correlate pressure altitude with temperature to form a temperature gradient. In another, the sensor platform has two temperature sensors, allowing the system to calculate temperature gradients. In another embodiment the sensor platform has sensors mirrored on the top and bottom so that accurate measurements are taken despite the orientation of the outlet that the sensor is plugged into.

In another implementation, the sensor platform may also sense Carbon Monoxide, VOCs, Carbon Dioxide, humidity, or air quality. In yet another, they may only sense temperature. In yet another, they may include audio sensors, motion sensors, infrared sensors, an accelerometer, or a gyroscope (solid state or otherwise). In yet another, they may include video or other optical sensors. In several embodiments, the motion, Carbon Monoxide, Carbon Dioxide, acoustic, optical, or other sensors may be designed to detect occupancy. Thus, detection and manipulation/control of any of the aforementioned environmental variables is within the scope of the invention.

In one embodiment, the communication subsystem may also act as a WiFi repeater to increase WiFi coverage, or a repeater for any other wireless protocol employed as part of the main communication system used in the system. In another embodiment, the sensor suite may deploy a WiFi network and act as a hub for the system. In certain embodiments, it is preferred that particular sensors be wall-mounted, and, thus, stationary, while other sensors be portable.

Figure 20:
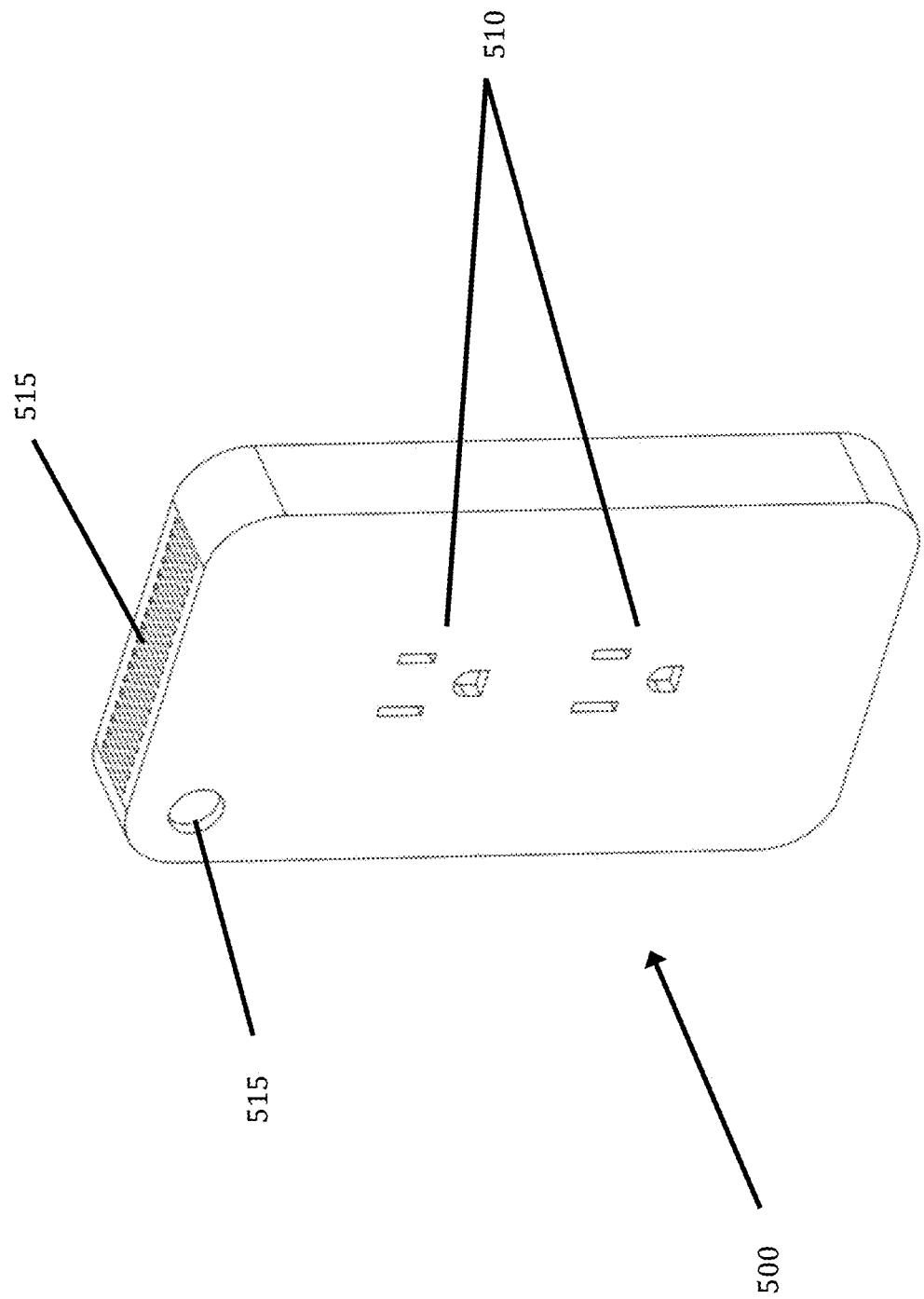
FIG. 20 illustrates a front perspective view of a pass-through sensor according to an embodiment of the invention.
Figure 21:
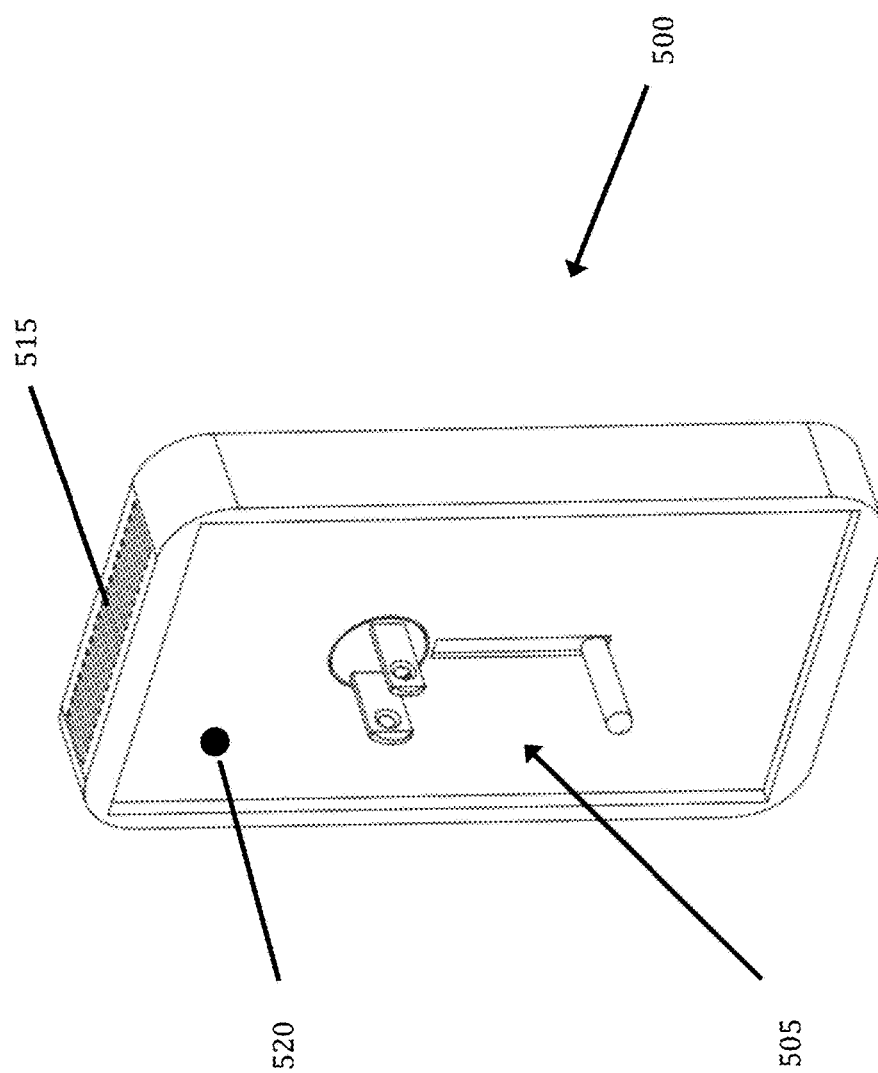
FIG. 21 illustrates a rear perspective view of a pass-through sensor according to an embodiment of the invention.

FIGS. 20 and 21 show one implementation (500) of the sensor platform (201). Sensor device (500) derives its power from a wall outlet using a standard plug (505). In another implementation, a sensor platform includes batteries. In yet another, they may be light-powered. The Power Subsystem (309) ensures that regardless of the source of power, the sensor platform itself receives clean power so as not to compromise the accuracy and precision of the sensors installed.

In one embodiment, the power subsystem (309) may also supply a number of USB Ports to allow the user to charge devices.

In one implementation the sensor platform (309), as shown in sensor device (500), includes pass-through plugs (510) so that when the user installs them, they do not lose an outlet within their home. Optionally, sensor device (500) has openings (515) that provide access to sensors within the device.

In another implementation the sensor platform may provide wireless control of the pass through plugs individually.

In another implementation the sensor platform may have modules to expand its capability that are attachable via an exposed port such as USB (not shown). The expansion module may include additional sensors, networking, processing, or other capabilities.

As mentioned above, the communication system is Wi-Fi (802.11), however in other embodiments can include Zig-Bee, 802.15, Z-Wave, Analog RF, Bluetooth or infrared or hard wired communication.

The next component is the Router and Processor, as seen in FIG. 5.

In one embodiment, we can install our own router and processor (203). This device is a router that deploys a wireless network. It may also connect to the internet with the communication system. This device may include our code already integrated, or packaged with a small computer or microprocessor that houses our firmware.

In another embodiment the sensors use their onboard capabilities to provide the routing and processing capability. In this embodiment a single sensor may act as the router and processor or the tasks may be distributed automatically and dynamically amongst the installed sensors.

In another embodiment, code is integrated on an existing wireless network by integrating it into existing compatible routers, and use that to integrate our devices. In all embodiments, any of the protocols mentioned earlier may be deployed.

In one embodiment, the processor and firmware (320) for the router and processor (203) houses the algorithm and control system, communication capabilities (319), and a power supply (321). The algorithm, and control system offers multiple modes. One mode is the installation mode, which enables the user to install the system. Another mode is the operation mode, where the algorithm receives stimuli from all the sensors platforms installed (201), the vents (200), the thermostat (202) and the control interface (204) to optimize operation in the home. The installation mode is described later in this document. The operation mode algorithm flowchart is presented in FIG. 7.

This operation mode algorithm may take into account all the variables mentioned earlier, such as humidity in each room, temperature in each room, motion in each room, vent state in each room, as well as other variables including but not limited to: location of sun, local outdoor weather, number of windows in the room, location of the room, and cloud cover among others. This algorithm may also take into account user preferences, which include but are not limited to: comfort zones, priority, schedule, and location. The algorithm is complex enough to learn and has variables necessary for successful home or building optimization, and future growth, but simple enough to implement and execute.

Figure 4:
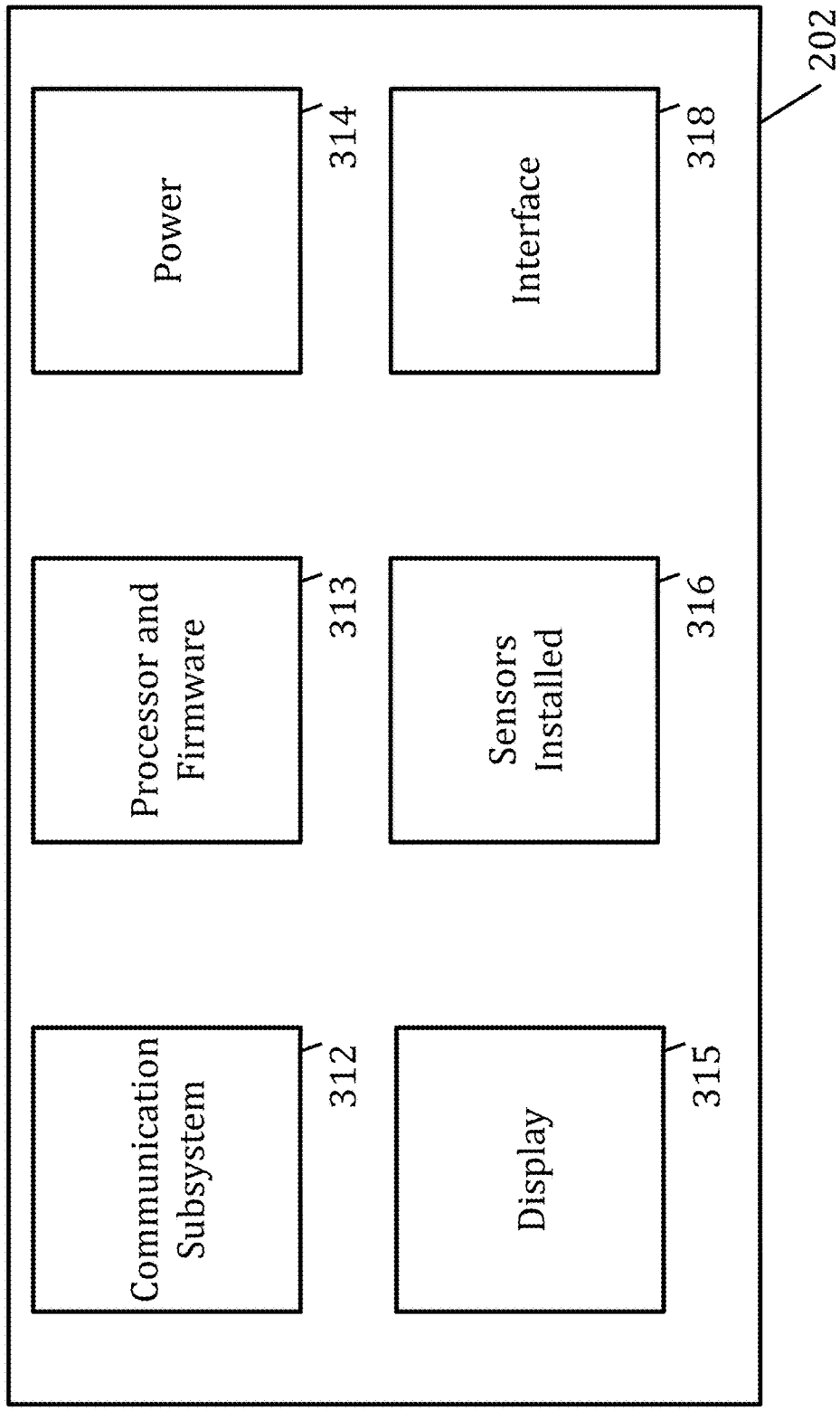
FIG. 4 illustrates an overview of a thermostat according to an embodiment of the invention.

The next component in the system is the thermostat as seen in FIG. 4.

In one embodiment the thermostat can be mounted on a wall and includes a power system (314) to provide power, processor and firmware (313) to process data and instructions given via the Communication (312) or the interface (318). In one embodiment there is a display (315) used for status and message reporting. The thermostat is used to control the HVAC system in response to stimuli received from the main router and processor (203) via the operation mode algorithm. Optionally, the thermostat (202) may include one or more onboard sensors (316), as described in connection with the sensor platform (201).

In one embodiment, the Thermostat features an e-paper or similar display to minimize power draw. The thermostat on the wall can also be controlled via the control interface (204) rather than the Router and Processor (203).

In yet another embodiment, the thermostat may be another device which includes an API (Application Programming Interface) to allow remote control of the device by our system.

In yet another embodiment, the user may not replace the thermostat but prefer manual control as given direction by the system through the control interface.

In yet another embodiment the system may not interact with the existing thermostat and only respond to predicted performance of that thermostat.

The final component is the control interface (204), shown in FIG. 6. In one embodiment, the control interface includes a communication subsystem (323), a power subsystem (325), a display (327), custom firmware or software (328) and a user interface (UI)(329). Optionally, instructions to support an installation mode (324) can be included or can be part of the custom firmware (328).

In one embodiment the control interface is a 10" (or equivalent) Android tablet, with a custom application loaded on with a custom android rom. In another embodiment, the user may use their own device running a custom native or web based application.

The device has multiple functions. The first is the installation mode (FIG. 8) as described in the following sections, enables a novel method of using the control interface as a feedback device to instruct a user through system installation.

Figure 7:
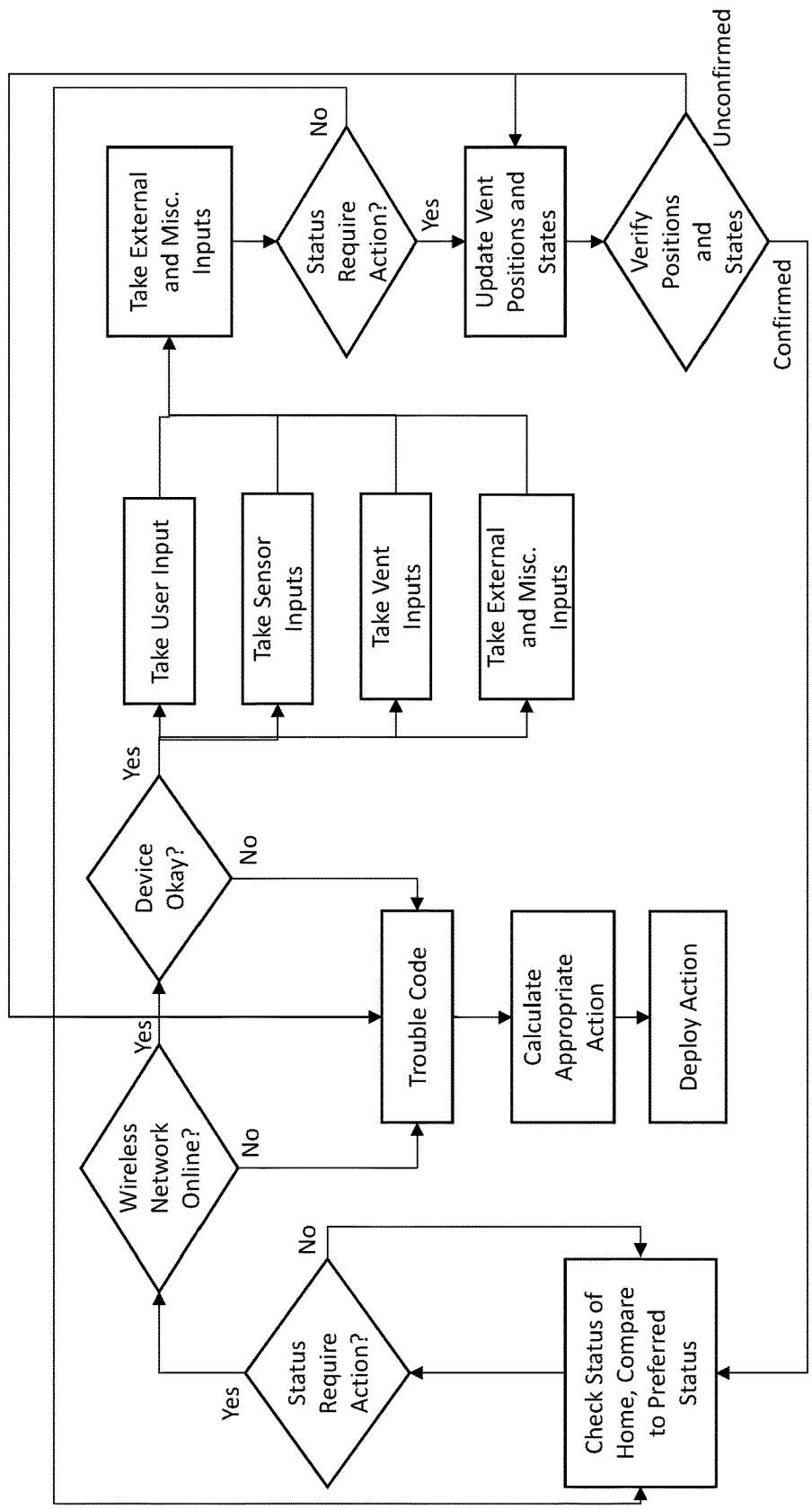
FIG. 7 illustrates an operational mode routine according to an embodiment of the invention.

Another function is to configure the control interface to allow the user to control the system, denoted Operation Mode (Algorithm Flow presented in FIG. 7). The UI (329) of the Control Interface produces multiple screens to allow control of the system using custom firmware. The device communicates with the Router & Processor through the communication sub system, (323) which uses WiFi or one of the other embodiments mentioned above.

In one embodiment the control interface allows the user to see all the zones in their home, multiple statuses (such as motion, temp and humidity) and set schedules and priorities for the system. In one embodiment, the system allows the user to set modes for the home, and see status from all the components the system controls.

In another embodiment, the user may select an automated zone where the system calculates everything by querying the user on comfort.

In another embodiment, the system operates and calculates the ideal state based on occupancy. In another embodiment, the user may use the tablet device to set occupancy manually. When determining what adjustments are needed to attain the desired conditions in the one or more rooms or spaces in a building, the system can send airflow values to be maintained by the one or more vents in the building or can provide relative feedback, e.g., that one or more vents needs to open more or close more relative to its present setting.

In yet another embodiment, the system may be configured to pick the best configuration to save the most energy.

In one embodiment, this interface also provides status to the user regarding the battery life of devices, communications status, and the overall health of not only the system, but the systems it controls (i.e. update the user on potential faults within their existing HVAC system).

In one embodiment, the supplied tablet device is open for use by the user as a conventional Android tablet.

In the Installation Mode (FIG. 8), the supplied control interface is used as a feedback system for installing the rest of the system. While this embodiment focuses solely on how aspects of the system are used in setting up the system itself, the same principles are applied to many different applications, such as installing appliances, TV's, computers and computer equipment, sound systems, even self-assembled furniture. For instance, imagine the installation of a new TV. When performing the install of the TV, an application on the phone would be employed to aid installation. When you plug the TV in, it finds the devices (through a wireless protocol such as WiFi), then provides instructions on how to install it. For instance, if you want to install a cable box, it walks you through which cables to install, and what to press on the remote. Essentially because the TV can communicate with the installation App, it can walk you through the installation step by step.

The embodiment presented in FIG. 1 describes the architecture necessary for using the Control Interface as an installation device. In this embodiment, the control interface receives stimuli from the Router & Processor—which is the key installation feedback stimuli. In future embodiments, the vents and sensor platforms are substituted. In other embodiments, no other devices may be used, by simply using the camera or other sensors on the Control Interface, the system can surmise correct installation steps as defined by user manuals.

FIGS. 8-12 present flow charts for the installation mode as it applies in this embodiment, for installing a specific embodiment of this system.

Figure 8:
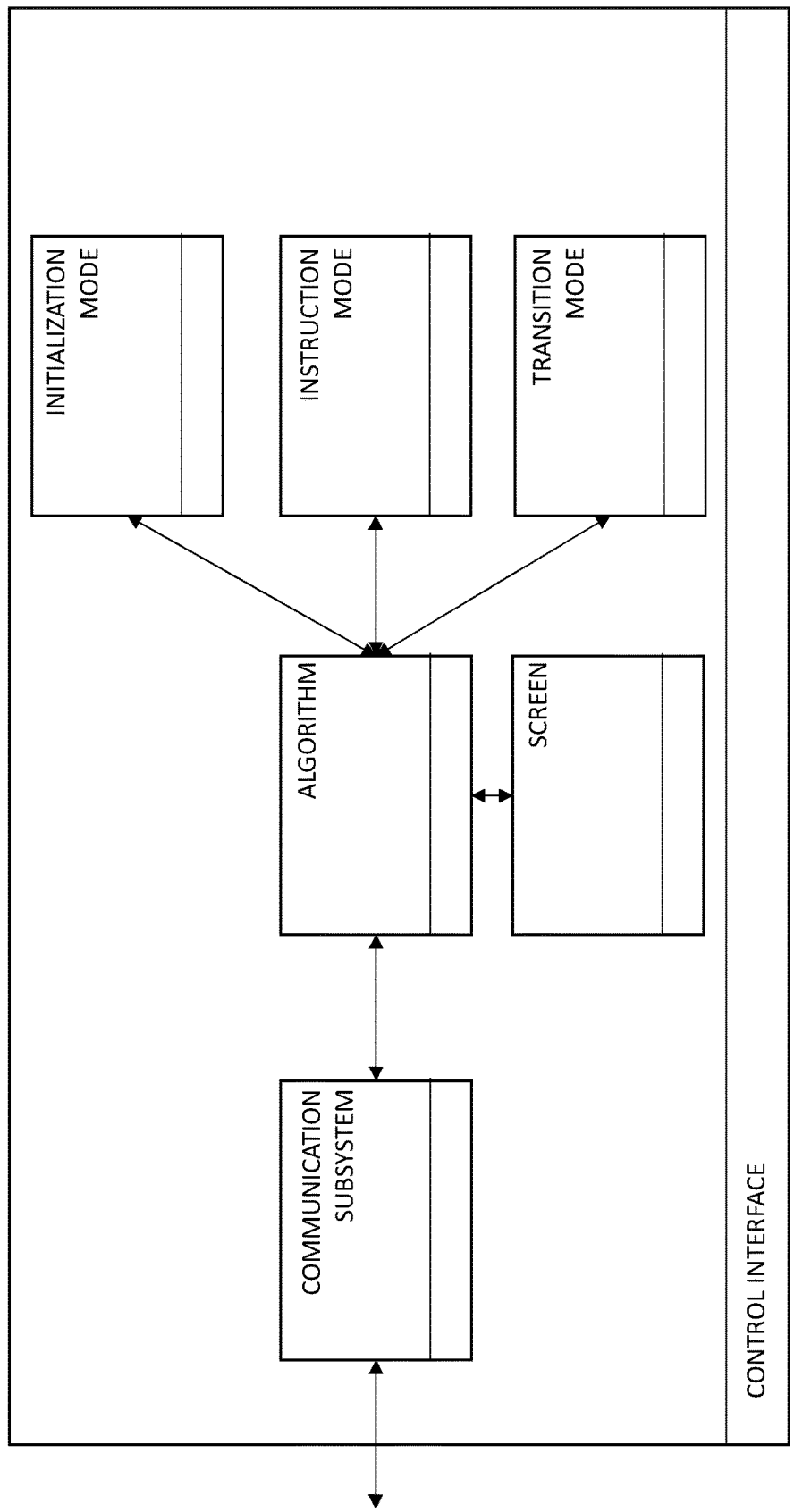
FIGS. 8-12 illustrate an installation mode routine according to an embodiment of the invention.

In FIG. 8 is the configuration step of the control architecture. In this embodiment, the system boots into a screen asking the user to enter initialization mode. The device has a custom application running which hosts the necessary algorithms for installation of this system.

Figure 9:
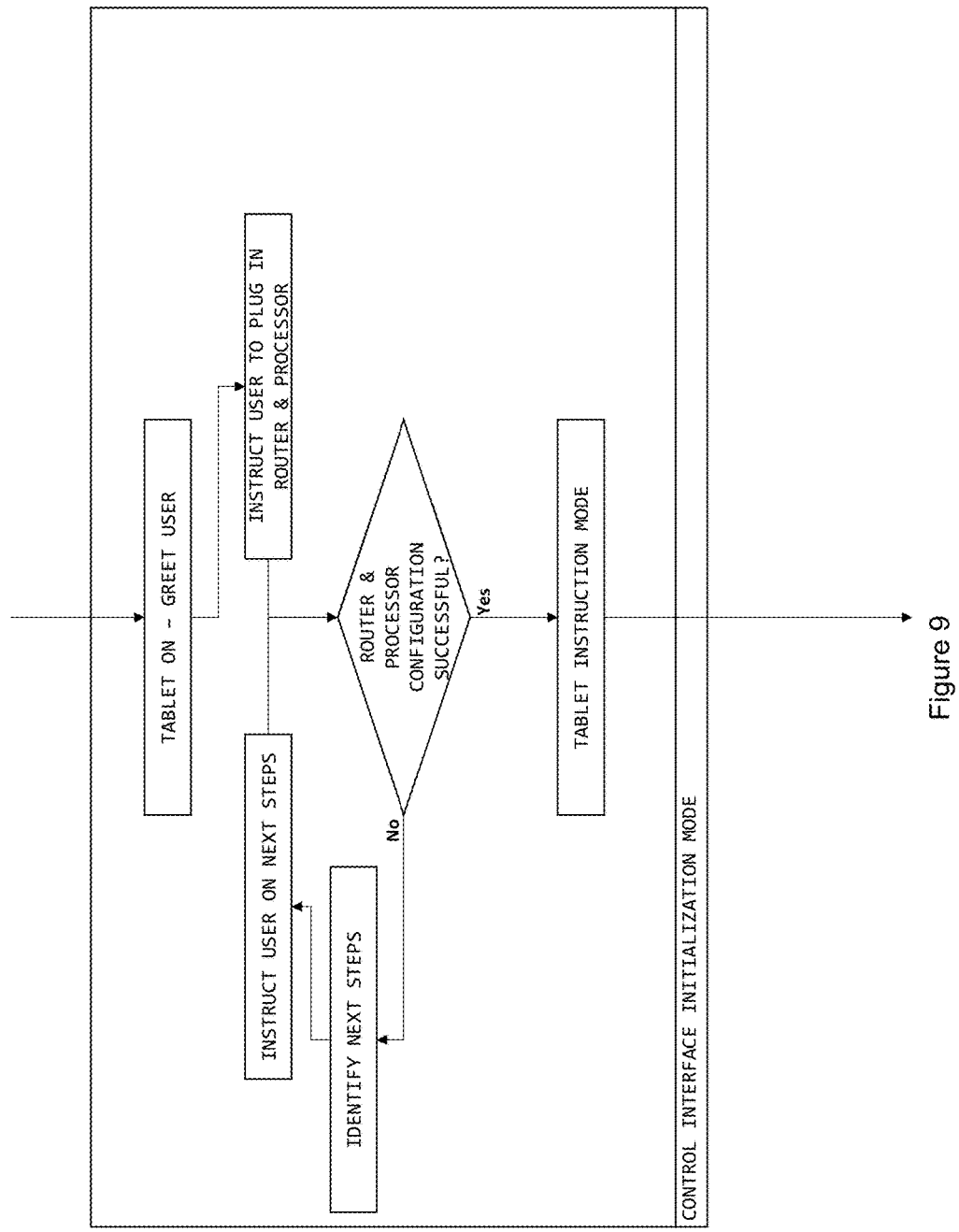
Figure 10:
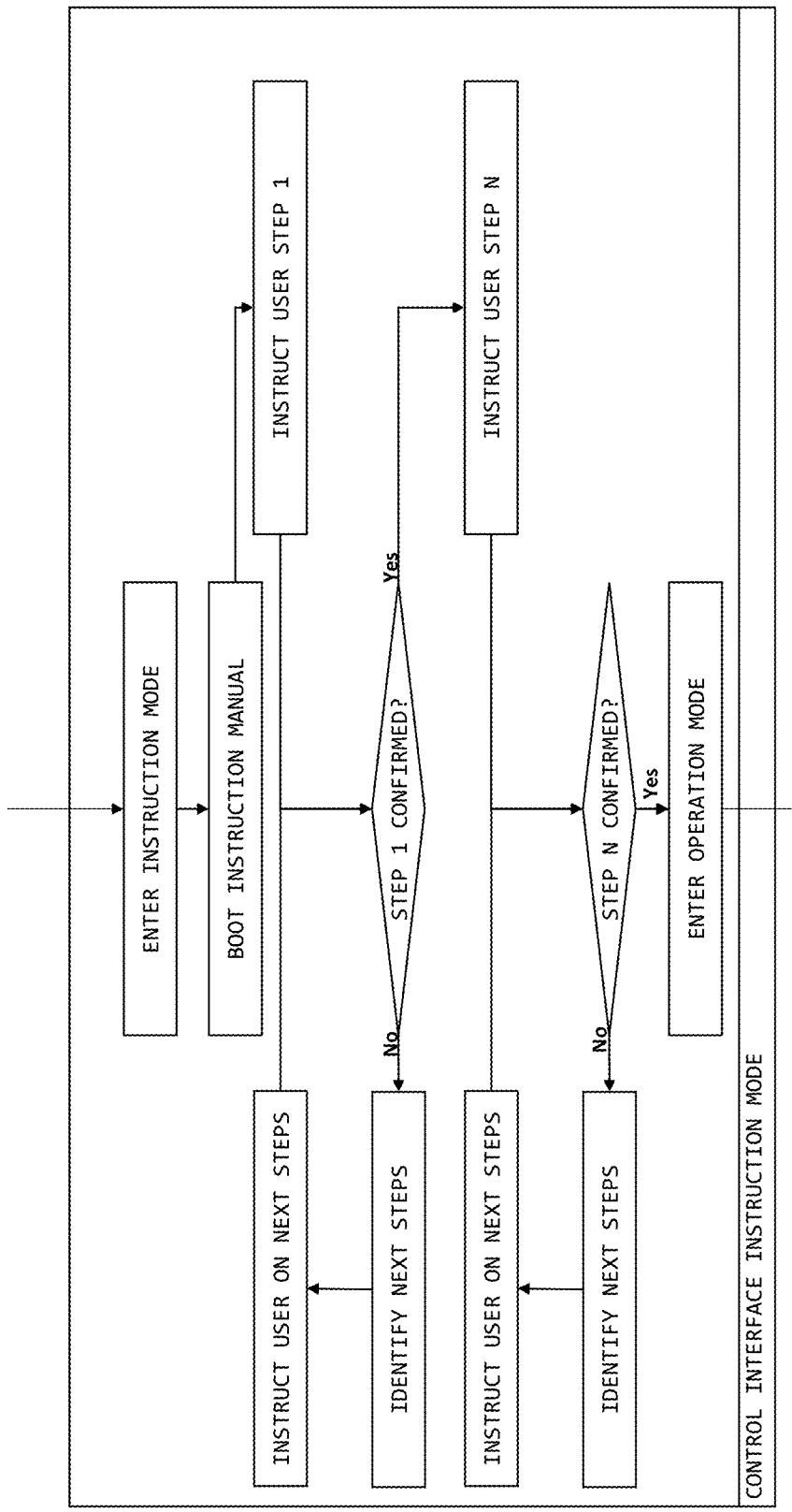

FIG. 9 describes the Initialization mode, where in this embodiment, the tablet is turned on and it greets the user. It then instructs the user to set up the wireless network or plug in the Router & Processor in this case. Once it is set up, the tablet confirms that the configuration was successful and enters the instruction mode. If the configuration was not successful, the router identifies the next steps, then instructs the user to execute them and tests the configuration again. Once the configuration is confirmed, the tablet enters the instruction mode.

Figure 11:
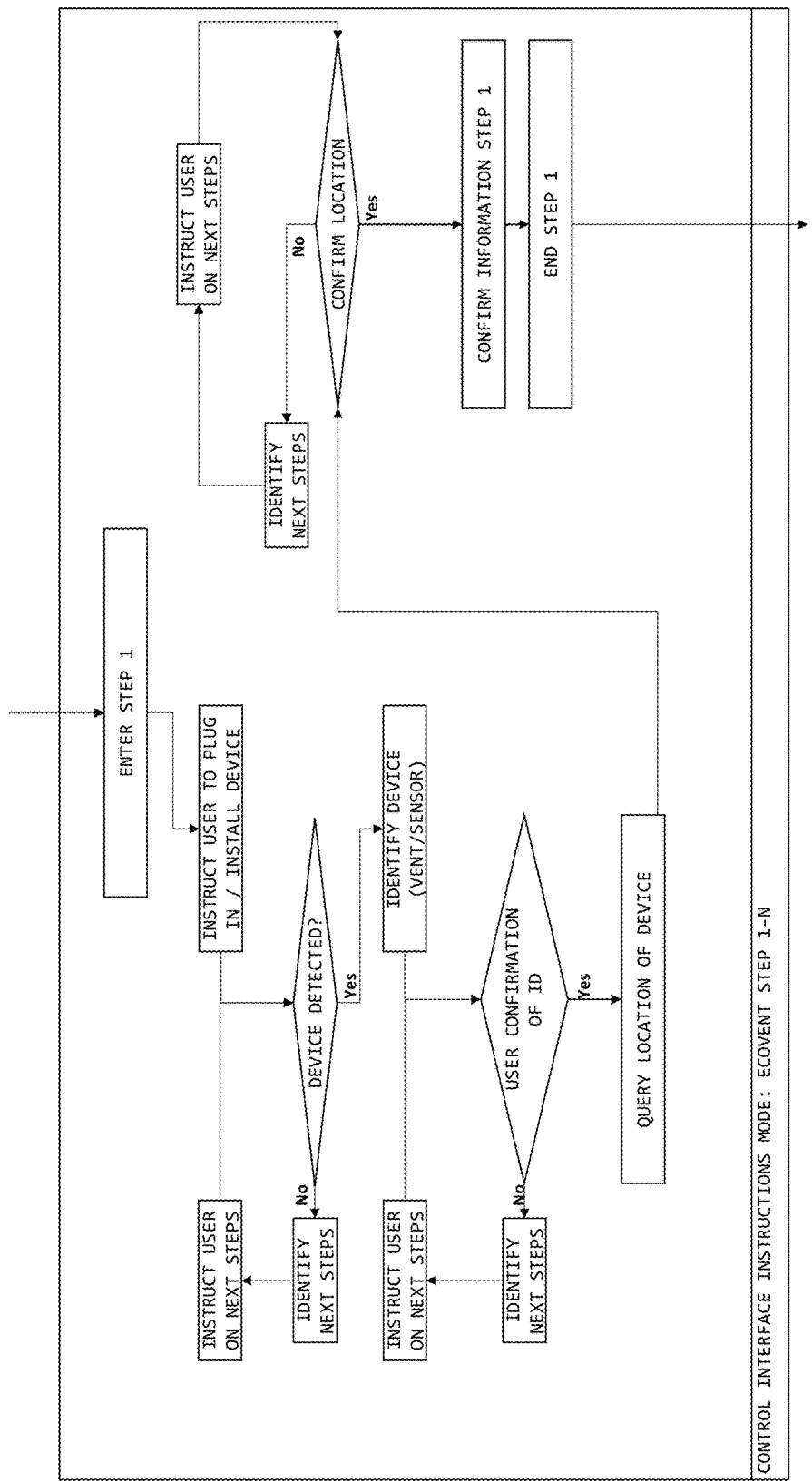
Figure 12:
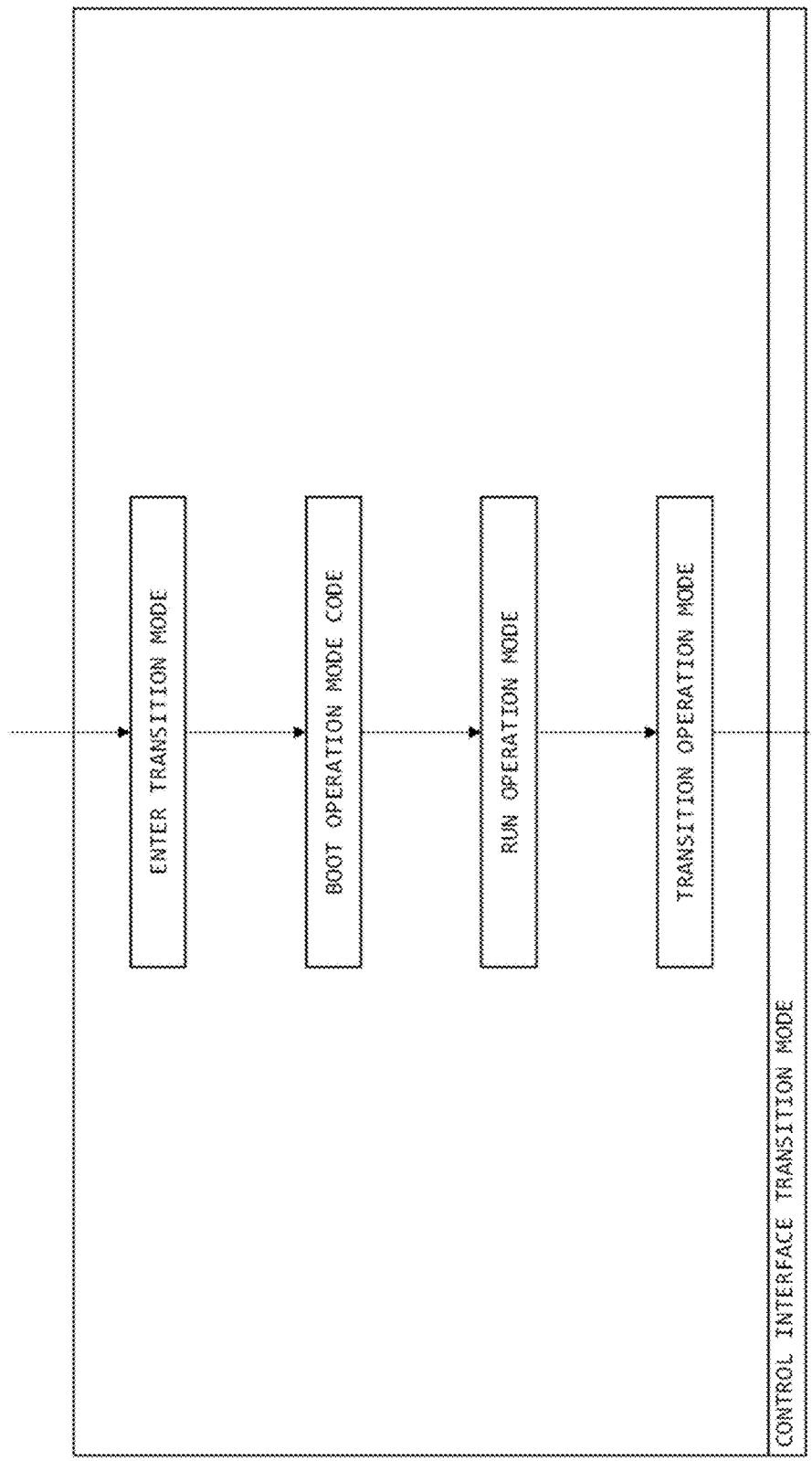

In this embodiment, the instruction mode (FIG. 10) boots the instruction manual, or in this case a specific set of software, and enter step 1 (as described in FIG. 11). It then confirms step 1. If successful it moves to the next step, if not, it selects the applicable course of action, and instruct the user on those steps. It then retries the confirmation of step 1.

In this embodiment, FIG. 11 describes the logic behind each Step (in this case Step 1). The system enters Step 1, as defined in FIG. 10, the Control Interface instructs the user to plug in one of the other devices (such as a vent, or sensor platform). It then attempts to detect the device and if successful, identify the device. If the detection is unsuccessful, the system determines the correct course, instruct the user and try the detection again.

In this implementation, after the device is detected, the system identifies the type of device, and confirms with the user. If the confirmation matches, the system then moves to location. If it doesn't match, the system identifies the next steps, instructs the user then tries to confirm the identification again.

In this embodiment after the device is identified and confirmed, the system queries the user about the location of the device. The user enters the location, and the system confirms. If the confirmation is accepted, the system ends step 1 and returns to FIG. 10. If it is not accepted, the system determines the best next steps, and instructs the user, then confirms the location again.

Once Step 1 is confirmed, it repeats this process for every step defined in the instruction manual, until all steps are confirmed. It then moves into the operation mode as defined in step 13.

Once in operation mode the control interface switches to the operational interface behave as a control device as described previously, until further installation of devices is necessary.

Figure 22:
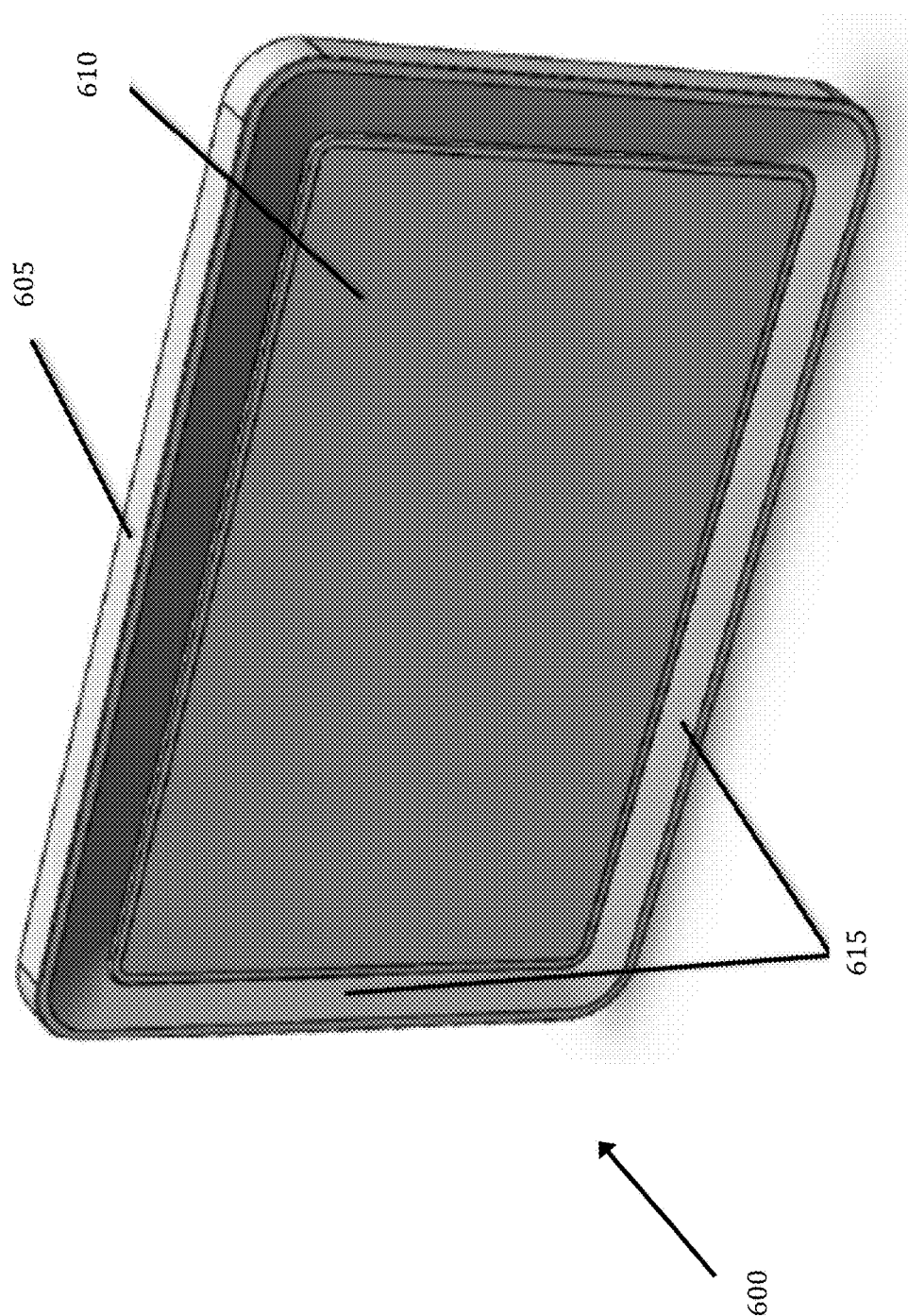
FIG. 22 illustrates a front perspective view of a faceplate assembly according to an embodiment of the invention.
Figure 23:
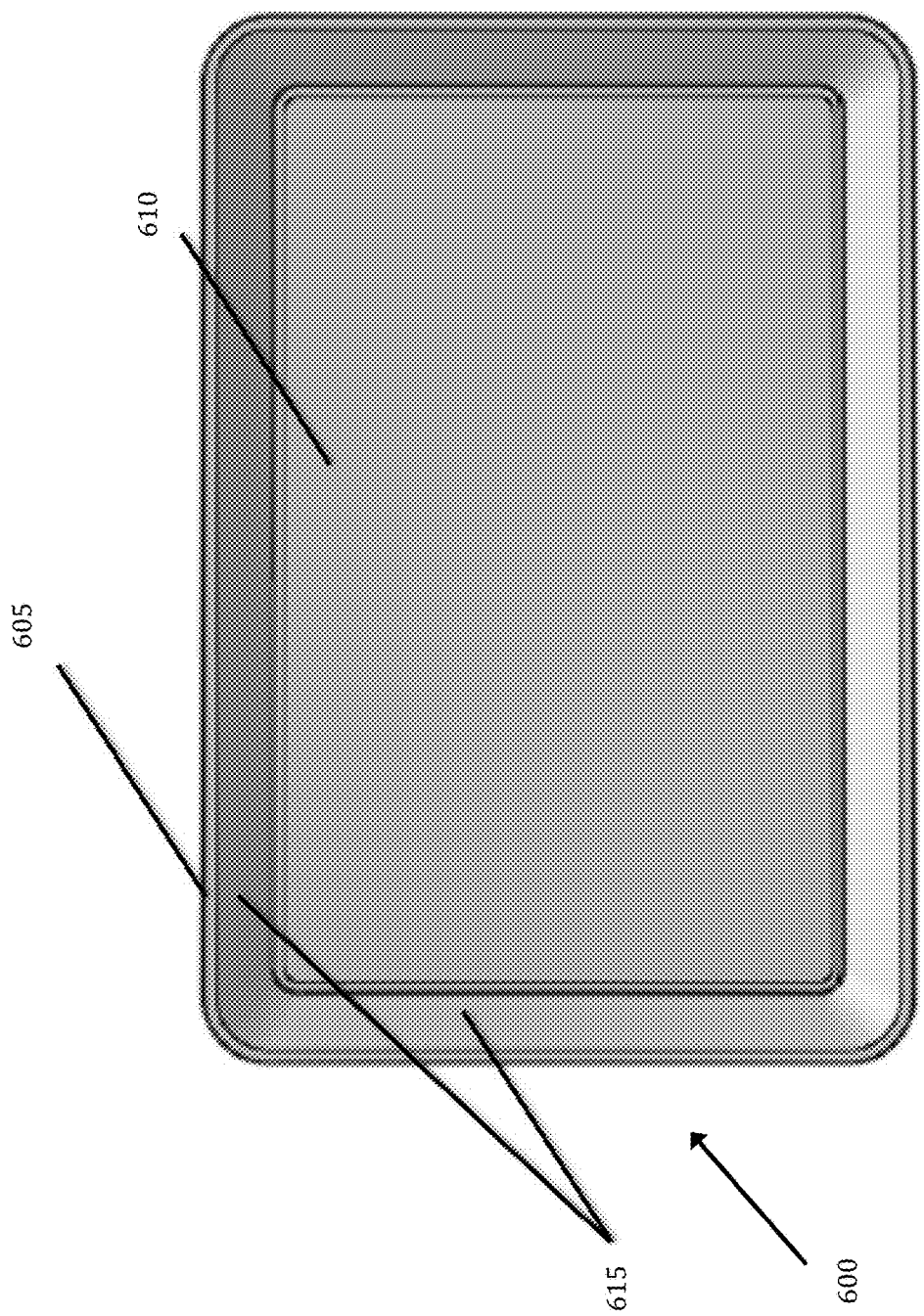
FIG. 23 illustrates a front view of a faceplate assembly according to an embodiment of the invention.

FIG. 22 illustrates a front perspective view of a faceplate assembly 600 according to an embodiment of the invention. The faceplate assembly 600 has a bezel 605 and a deflector plate 610. The deflector plate 610 is spaced apart from the bezel 605 to define an annular passage 615 between the space behind the faceplate and the space in front of the faceplate. FIG. 23 illustrates a front view of the faceplate assembly 600.

Figure 24:
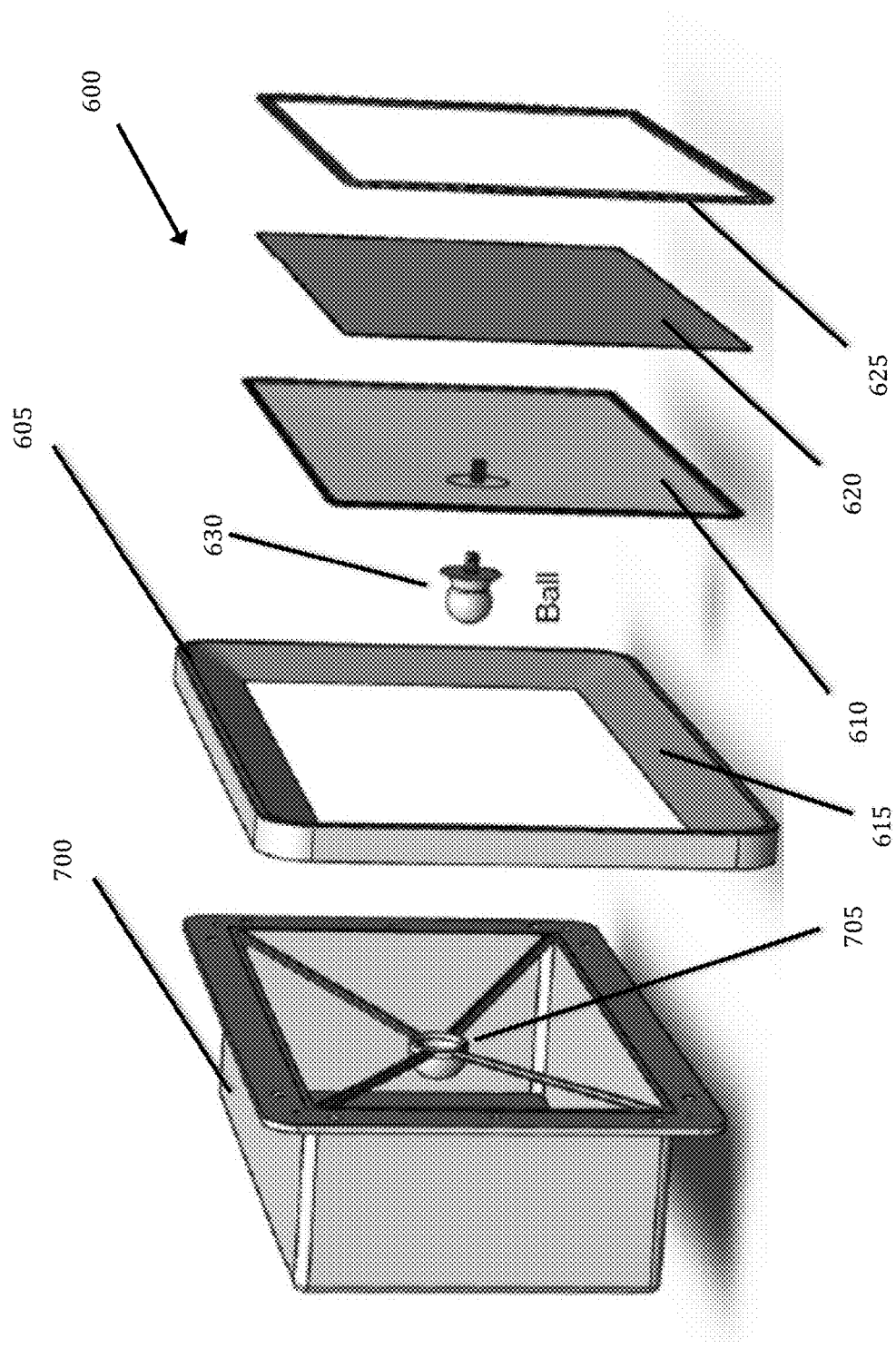
FIG. 24 illustrates an exploded perspective view of a housing and faceplate assembly according to an embodiment of the invention.

FIG. 24 illustrates an exploded perspective view of a housing 700 and the faceplate assembly 600 according to an embodiment of the invention. FIG. 24 shows the deflector plate 610 separate from the bezel, revealing an angled bevel 615 of the deflector plate 610. The figure also shows an optional interchangeable inlay plate 620, which can impart a decorative aspect to the deflector plate 610. The figure also shows an optional edge material 625, which is applied to the deflector plate 610 and surrounds the edge of the deflector plate (described in more detail below).

Figure 25:
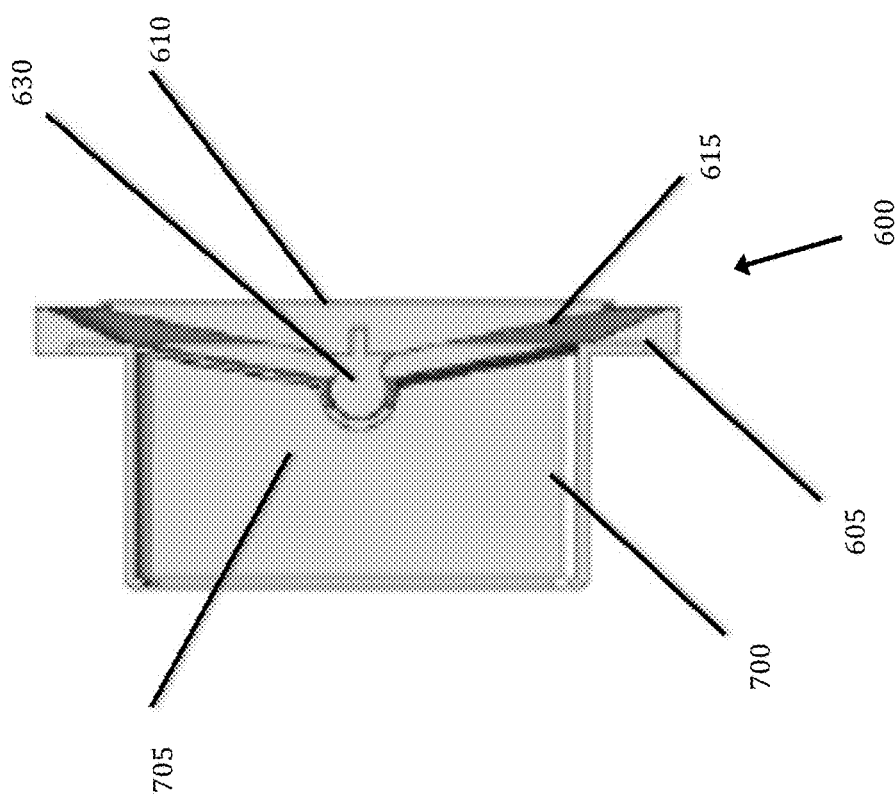
FIG. 25 illustrates a cross-sectional side view of a housing and faceplate assembly according to an embodiment of the invention.

A ball pin 630 is removably attached to the back surface of the deflector plate 610. The ball pin 630 fits into socket 705 that is part of the housing 700. The ball pin 630 and socket 705 cooperate to hold the deflector plate 610 apart from the bezel 605. FIG. 25 illustrates a cross-sectional side view of the housing 700 and the faceplate assembly 600. This figure shows the cooperation between the socket 705 of the housing and ball pin 630 attached to the deflector plate 610 that provides the spacing to define the annular passage

Figure 26:
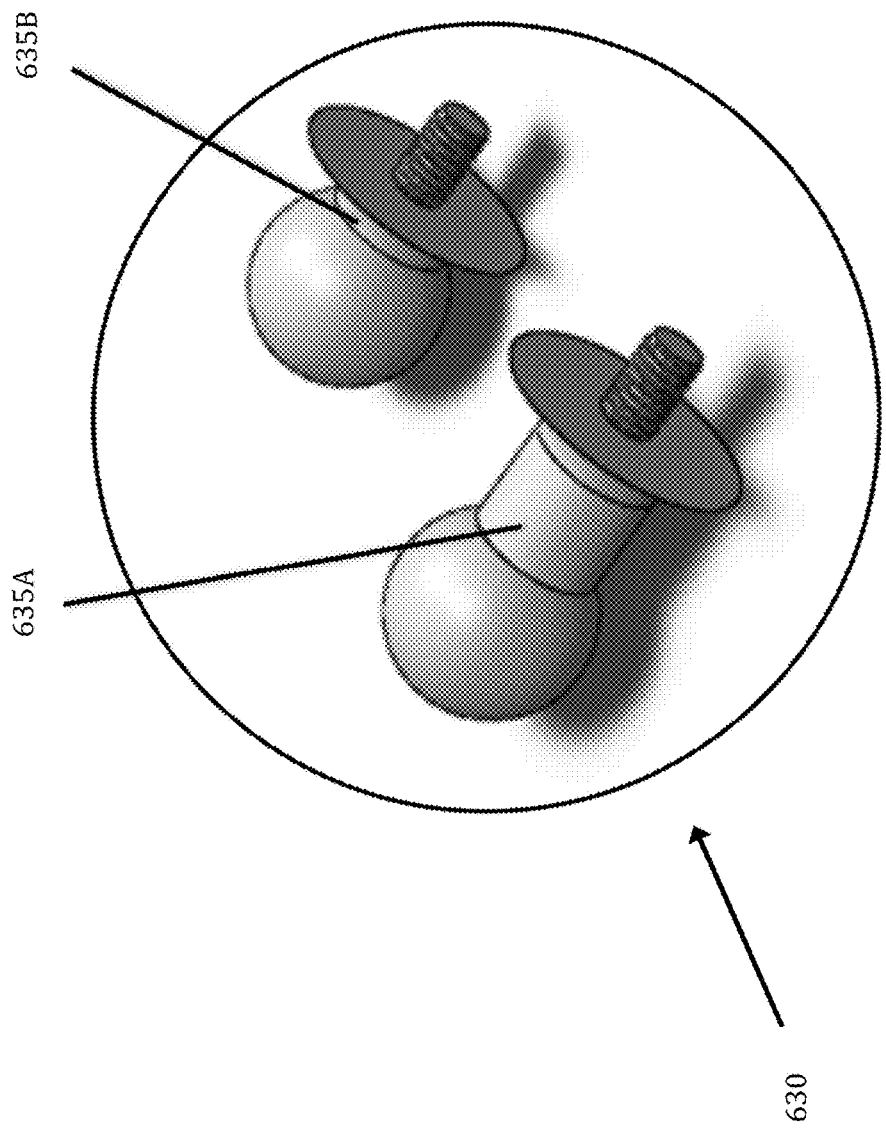
FIG. 26 illustrates a perspective view of two ball pins according to an embodiment of the invention.

615. In addition, this figure illustrates how the bezel 605 is attached to the housing 700. As described above, the bezel can be magnetically mounted to the housing or by using known methods of attachment, such as screws, adhesives, or clips that attach to the housing sides. FIG. 26 illustrates a perspective view of two ball pins 630 according to an embodiment of the invention. As shown in the figure, each ball pin has a neck portion 635. The ball pins are interchangeable and each can have a neck portion of different lengths. In one implementation of the ball pin 630, the length of neck portion 635A is relatively long, while in another implementation, the length of neck portion 635B is relatively short. Ball pins with relatively longer neck portions will define relatively larger annular passages 615 as compared to ball pins having relatively shorter neck portions.

Figure 27:
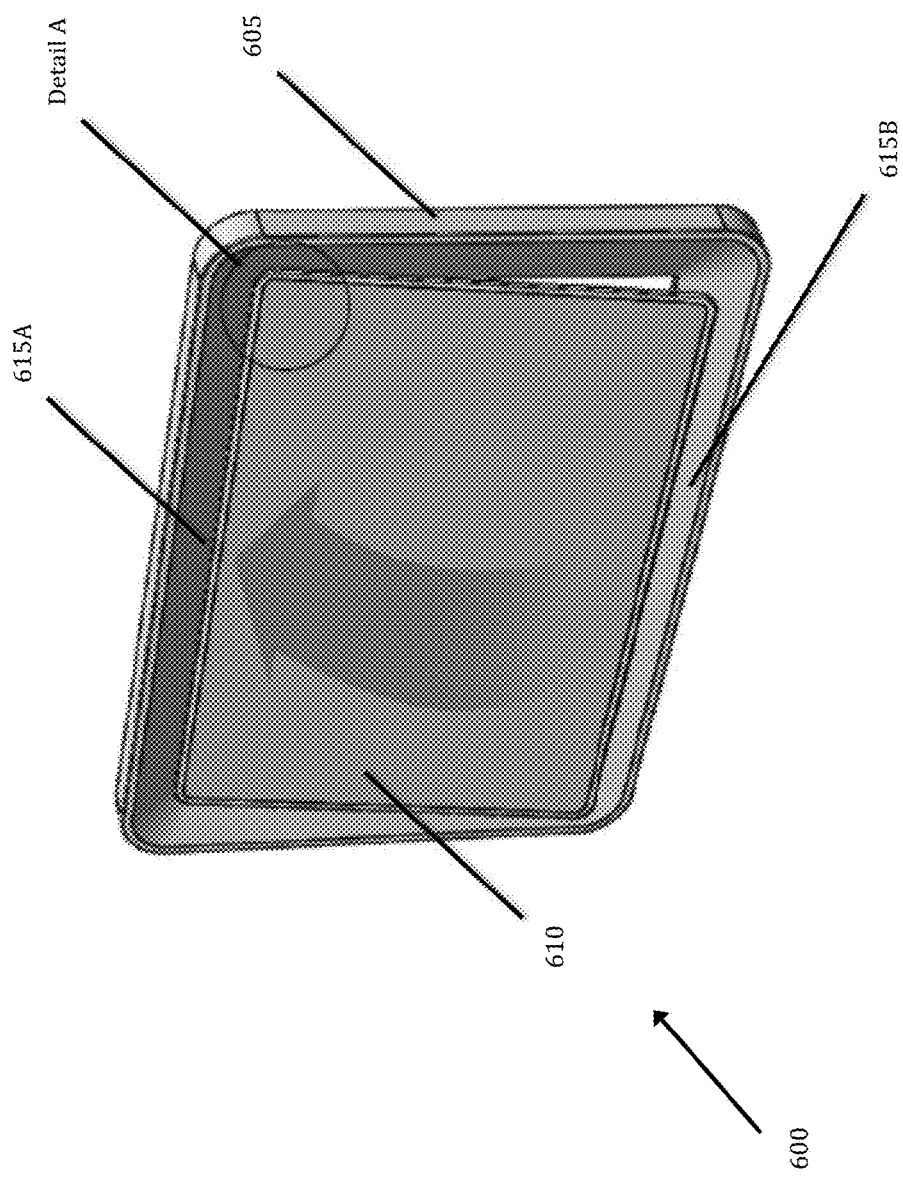
FIG. 27 illustrates a front perspective view of a faceplate assembly according to an embodiment of the invention.

FIG. 27 illustrates a front perspective view of the faceplate assembly 600. The ball pin and socket form a joint that enables the deflector plate 610 to be tilted relative to the bezel 605. When the deflector plate 610 is held substantially flat relative to the bezel plane, the annular passage 615 is open on all four edges of the bezel. This forms a 4-way vent that distributes air flowing through the annular passage in all four directions. When the deflector plate 610 is tilted upwards, the top edge of the deflector plate 610 contacts the top bevel of the bezel 605, thereby sealing off the top portion of the annular passage 615A. Meanwhile, the bottom portion of the annular passage 615B is opened more widely. In this way, the faceplate assembly 605 forms a directional vent when coupled to a housing present in the ductwork of an HVAC system. A user can direct air in the desired direction using the vent. In a rectangular implementation, tilting the deflector plate 610 towards its long edge creates a vent that directs air in predominately one direction (a 1-way vent), while tilting the deflector plate towards its short edge creates a vent that directs air in predominately three directions (a 3-way vent). Although only a rectangular implementation is shown and described, other shapes, such as square, circular, oval, triangular, and polygonal are within the scope of the invention.

Figure 28:
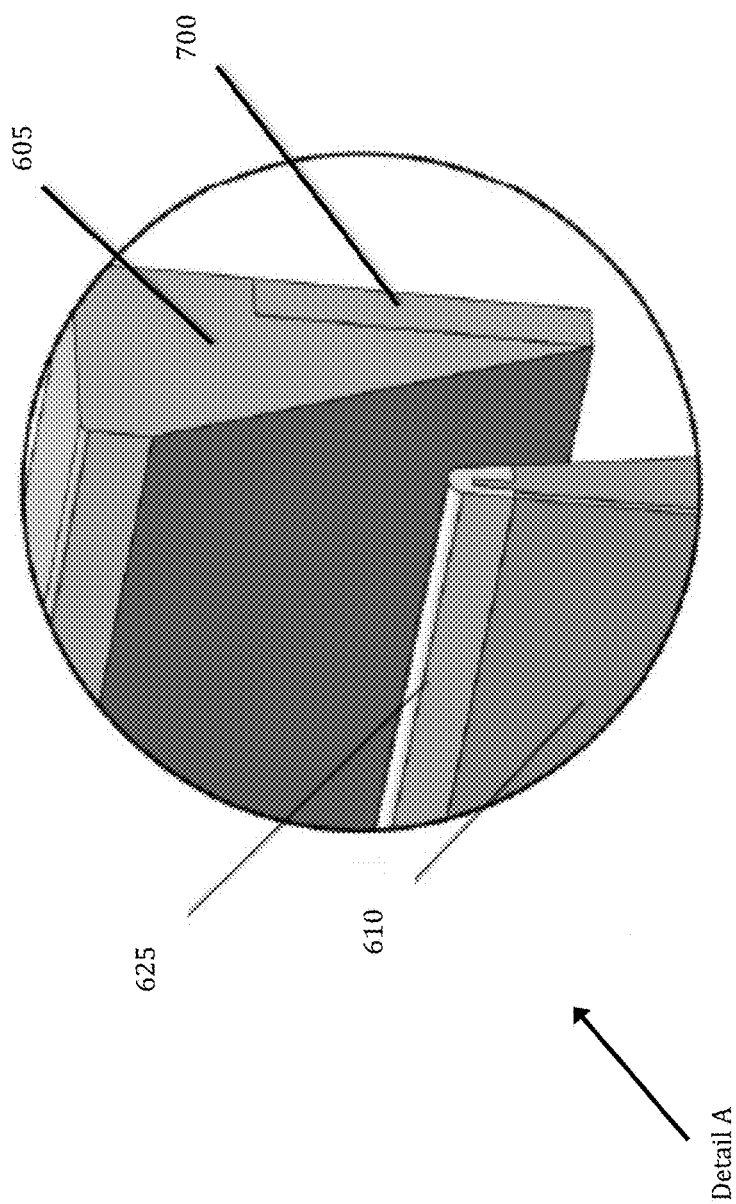
FIG. 28 illustrates detail A of FIG. 27.

FIG. 28 illustrates Detail A of FIG. 27. As mentioned above, an implementation of deflector plate 610 has optional edge material 625. Edge material 625 can be rubber, silicone, or any other pliable and resilient material to help create a seal between the edge of the deflector plate and the bevel of the bezel 605. Detail A also shows the mounting of the bezel 605 to the housing 700.

Embodiments of the faceplate assembly 600 offer less resistance to airflow than known vent/register faceplates. For example, simulations of the faceplate assembly attached to a housing of about 6 inches by 10 inches with a two-piece variable shutter mechanism were performed. The 1-way faceplates were modelled using a scoop design that directed air in predominately one direction. When compared to stamped steel register faceplates, the simulated faceplate assembly shows at least about a 25% less pressure drop at a flow rate of 98 cubic feet per minute at a velocity of 500 feet per minute (0.057 inches of water versus 0.076 inches of water). Meanwhile, simulations of the faceplate assembly compared to stamped steel register faceplates shows at least about an 8% less pressure drop at a flow rate of 208 cubic feet per minute at a velocity of 500 feet per minute (0.374 inches of water versus 0.409 inches of water). It is expected that some embodiments of the faceplates described herein will have at least about 5% less pressure drop compared to stamped steel register faceplates. Other embodiments are expected to have at least about 10% less pressure drop compared to stamped steel register faceplates. While still other embodiments are expected to have at least about 15% less pressure drop compared to stamped steel register faceplates. Still further embodiments are expected to have at least about 20% less pressure drop compared to stamped steel register faceplates. Other embodiments are expected to have at least about 30% less pressure drop compared to stamped steel register faceplates.

Embodiments of the faceplate assembly 600 also produce less noise than known vent faceplates and are believed to encourage a more laminar flow condition than known vent faceplates. For example, simulations of noise produced by the 6 inch by 10 inch model faceplate assembly described were performed. When compared to stamped steel register faceplates, the simulated faceplate assembly shows at least about 11.8% less pressure noise at a nominal flow rate (75 decibels versus 85 decibels). It is expected that some embodiments of the faceplates described herein will produce at least about 5% less noise compared to stamped steel register faceplates. Other embodiments are expected to produce at least about 10% less noise compared to stamped steel register faceplates. While still other embodiments are expected to produce at least about 15% less noise compared to stamped steel register faceplates. Still further embodiments are expected to produce at least about 20% less noise compared to stamped steel register faceplates. Other embodiments are expected to produce at least about 25% less noise compared to stamped steel register faceplates. The percentage reductions of noise recited herein are intended as percentage reductions of decibel values.

Figure 29:
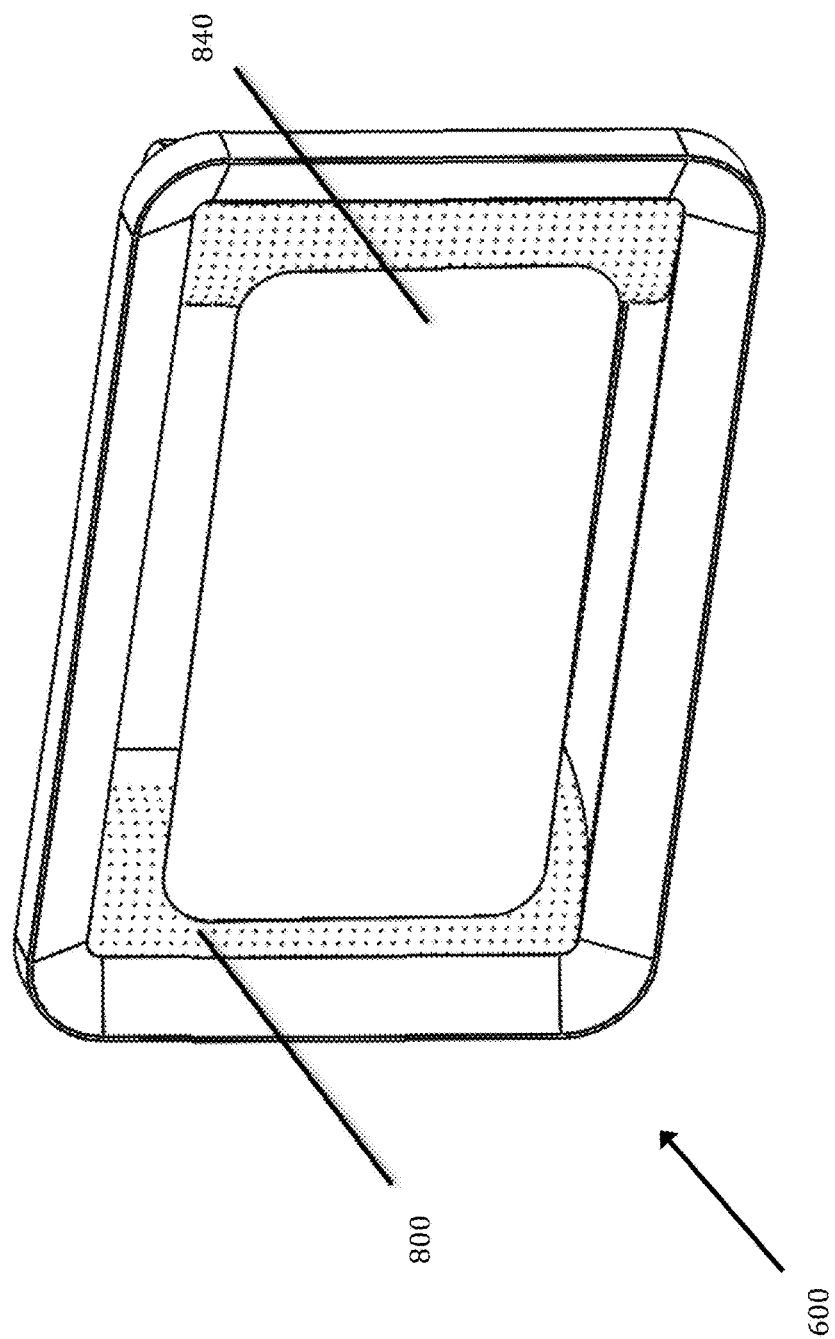
FIG. 29 illustrates a perspective view of a faceplate assembly including perforated surfaces for sound absorption.
Figure 30:
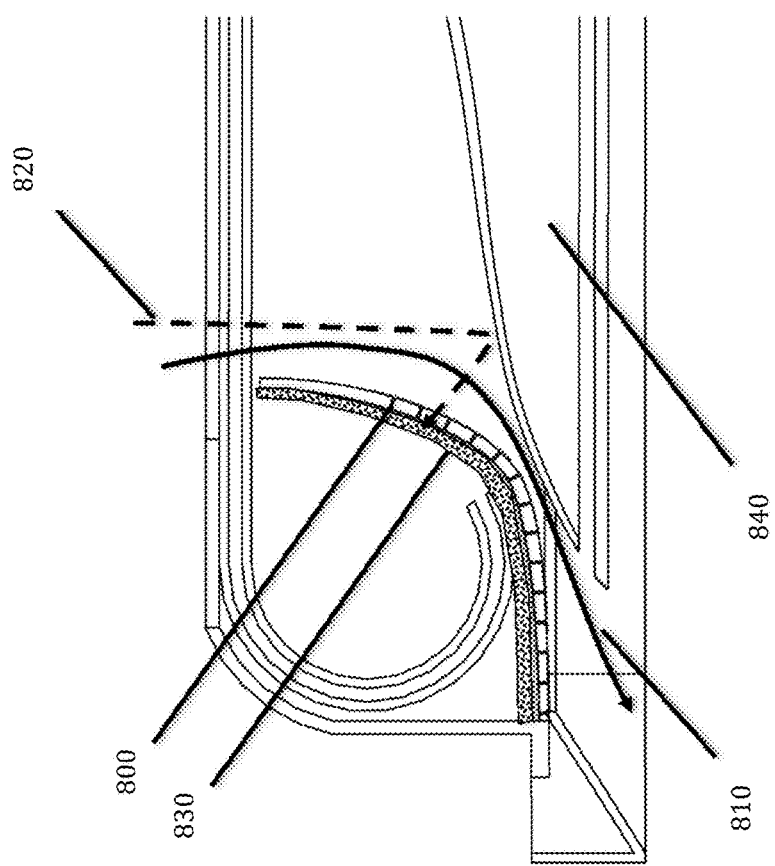
FIG. 30 illustrates a cross-sectional view of the left side of the faceplate 600 looking from top to bottom.

FIG. 29 illustrates a perspective view of a faceplate assembly including perforated surfaces for sound absorption. FIG. 30 illustrates a cross-sectional view of the left side of the faceplate 600 looking from top to bottom. In certain implementations of faceplate 600, the faceplate 600 is designed with surfaces that minimize noise conducted from the ducts to the room and the noise generated by the vent itself. In one embodiment, the faceplate 600 includes perforated diffusers 800 that minimize the disturbance to air flow 810 passing out of the faceplate into a space, while allowing sound 820 to pass through to a noise absorptive surface 830. The perforated surface 800 reduces the impact that the noise absorptive surface 830 has on the air flow. For example, under certain conditions, laminar airflow can be maintained. In another embodiment, a deflector plate 840 is designed to reflect duct noise 820 to the sound absorptive surface 830 such that the amount of sound energy passing into the space is reduced. Such a deflector plate also allows the air to be dispersed to the room without presenting a prohibitive pressure drop.

In certain embodiments, as shown in FIGS. 29 and 30, sharp corners and/or airflow paths with sharp transitions are reduced in the vent and/or faceplate surfaces exposed to airflow through the vent. Doing so reduces turbulence and noise generated by air flow through the vent.

In another embodiment of the invention, an application is deployed on a mobile device that connects to the system as a whole via the local network deployed by the system itself (e.g., the Router & Processor and/or one or more sensor assemblies acting as a network routing node) or via the Internet through a separate wireless router and/or a "cloud" service. In one implementation the application has decision making capability to automatically connect to the system through the preferred means.

In one embodiment any of the sensor platforms are battery powered devices, either designed as part of the system or utilizing sensors on another device, such as a smartphone or other portable computing device. In such an embodiment, the position of the sensor platform within the space of concern (e.g., a building) of the system as a whole is determined using a technology such as a Bluetooth or other wireless beacon or via sensor correlation. Techniques for determining the position of the sensor platform/mobile device based on Bluetooth or other wireless beacons are known to one having ordinary skill in the art. Meanwhile, the sensor correlation technique utilizes other known data about the space of concern to create a map of correlated environmental variables (e.g., temperatures, pressures, relative humidity, and other data such) so that the most likely position of a device detecting a particular set of environmental variable values can determined according to the correlated variables. For example, if the system as a whole has determined that a temperature gradient exists through the space, the temperature detected by the sensor platform/mobile device is used to position the device at the position having the closest matching temperature according to the gradient values. The environmental variables from the device can then be used by the system to provide comfort to the individual carrying the device. The location data may be fed to external systems as localization data of the individual.

In one embodiment, the system uses occupancy information to localize climate control based on a user profile associated with a mobile device. When the system detects a user entering or departing a room, the system may react to optimize comfort or economy. In one embodiment the system uses "Bluetooth Beacon" technology to track a user's location. When the location is determined to be in a room defined in the system, the control module can take appropriate action.

In one embodiment, the beacon information can be used to develop a map of the user's home. Utilizing multiple beacons throughout the home, in vents or sensors, the system can generate a point cloud of location data. This data can create a relative location map of rooms adjacent to one another. This information can be used to infer how rooms interact via airflow. This information can also reveal which rooms have outside walls, another important fact in supplying optimal comfort. The beacon data can also provide data on room volumes and any spaces not directly assigned to the system.

In another embodiment, localization is used during the installation process to automatically pair devices in the same room. Using the beacon information, the system can infer that a vent is being installed in the same room as an already installed sensor and pre-populate the app with the correct data.

In a further implementation, certain components employ a modular design that separates high voltage and low voltage components of a system that enables faster time to market due to accelerating the certification process. By separating the high voltage components of the design in a standalone housing, certifications can begin earlier, thereby shortening the time to market. This design also allows flexibility in implementing variations of the base design to include an extension cable or even international adapters without having to change the sensor design.

Figure 31:
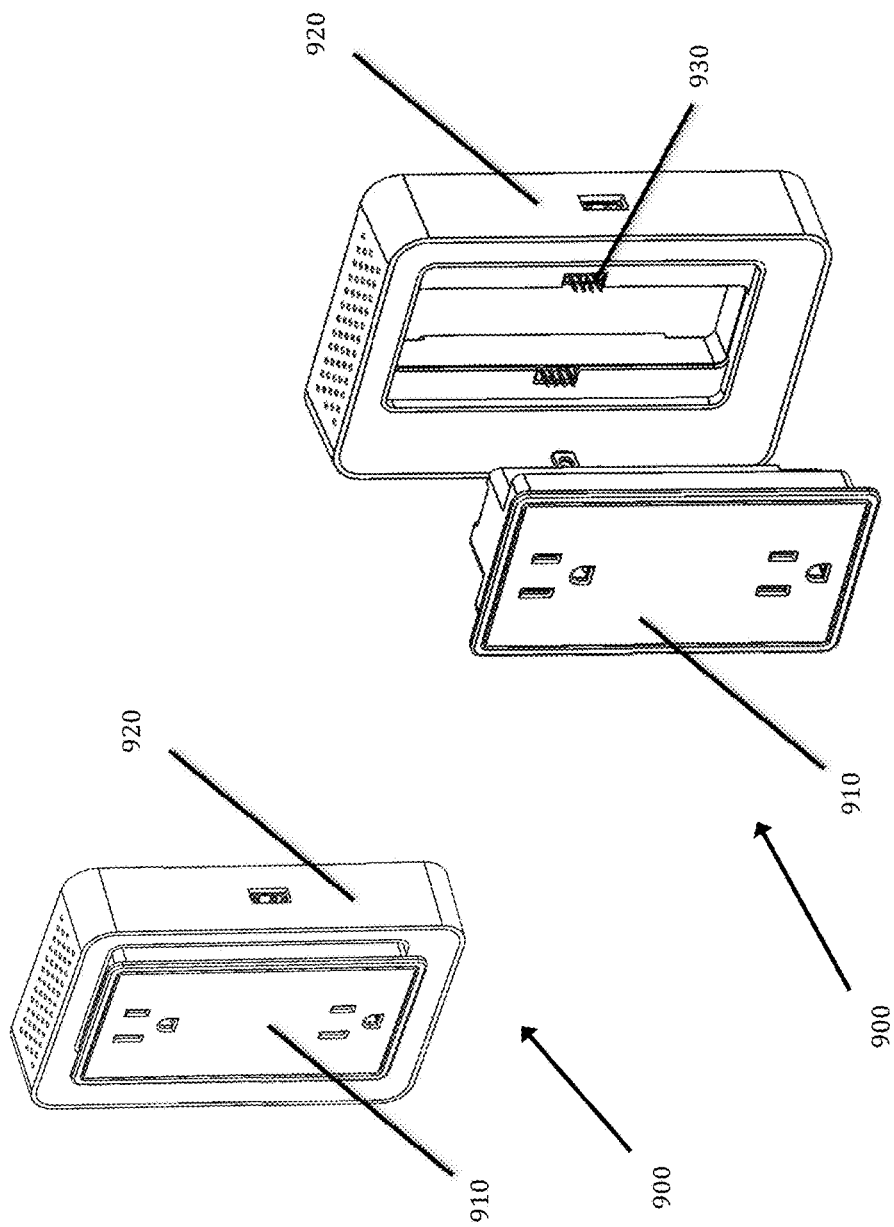
FIG. 31 illustrates modularity of a high voltage section of a wall sensor and an arbitrary orientation of a high voltage section in relation to a low voltage section.

FIG. 31 illustrates modularity of a high voltage section 910 of a wall sensor 900 and the ability to accommodate an arbitrary orientation of the high voltage section 910 in relation to a low voltage section 920. When the high voltage section 910 engages the low voltage section 920, complementary connectors enable the high voltage section 910 to supply low voltage power to the low voltage power section 920. The high voltage section 910 includes an appropriate power supply to supply the needed low voltage power to the low voltage power section 920.

Figure 32:
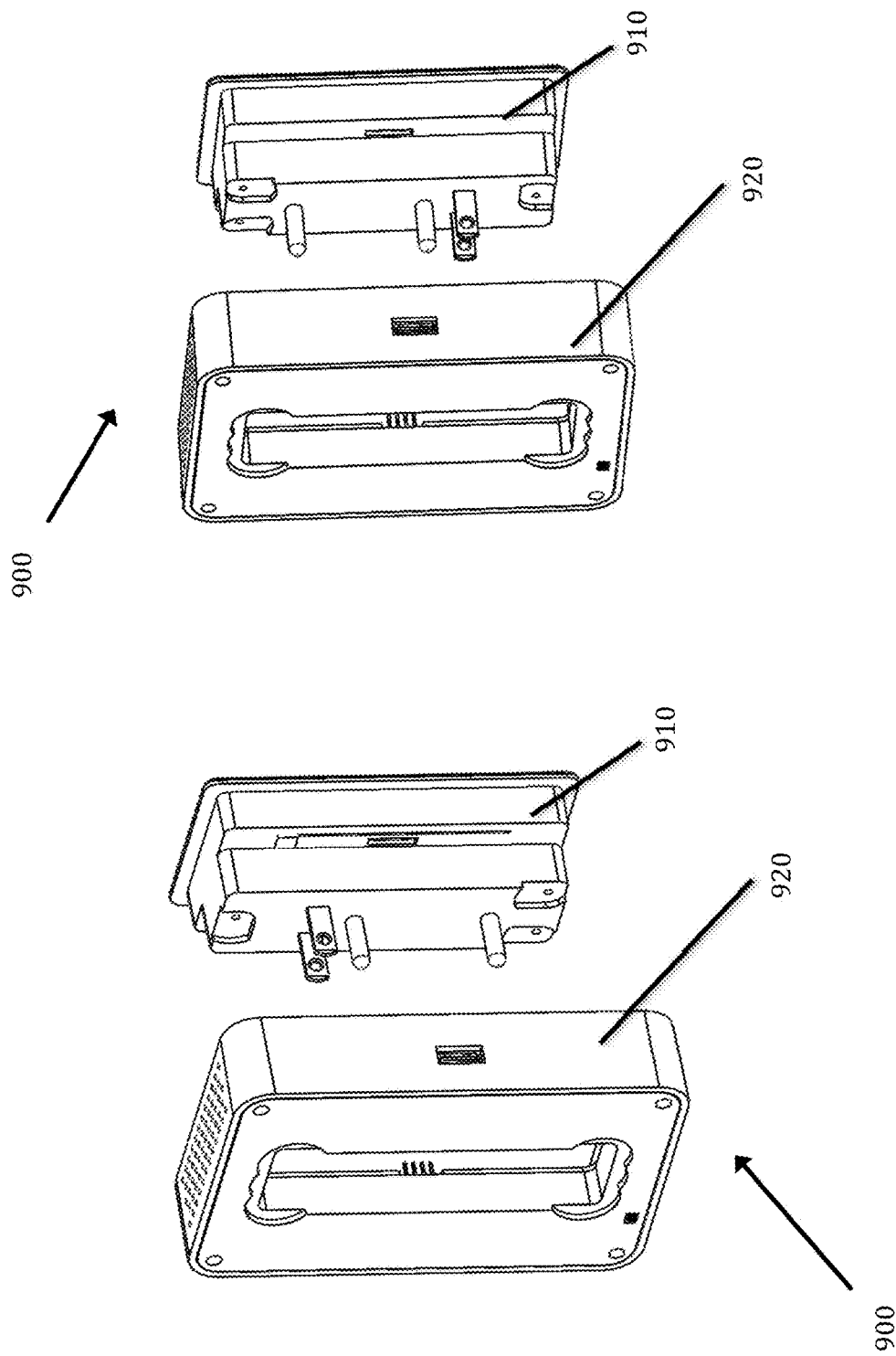
FIG. 32 illustrates an illustrative application of a modular design.

The modular design also enables an arbitrary orientation of the low voltage section 920 relative to the high voltage section 910. FIG. 32 illustrates an illustrative application of a modular design. For example, power outlets in the United States can be installed in one of two vertical orientations— either with the line and neutral slots above the grounding slot or with the grounding slot above the line and neutral slots. The modular design allows the high voltage section 910 to be oriented according to the orientation of the outlet, while the low voltage section can be maintained in the same vertical orientation. This design provides advantages for certain types of sensors that require a particular vertical orientation. For example, a climate sensor that measures temperature must be installed with the temperature sensing elements at the lowest vertical orientation to prevent skewing temperature data by heat from other components in the sensor. By utilizing the separate high voltage section 910, which can be flipped to match the outlet orientation, the sensor component of the device can remain in its vertical orientation. This aids in maintaining the accuracy of the sensor regardless of the orientation of the user's outlets.

As described above, an environmental variable gradient can be determined based on data from multiple sensor sources. In some embodiments, one or more gradients are used by the system to determine the value of an environmental variable at a particular location without the need to have a sensor present at the particular location. The environmental variable at that location can then be controlled by the system. For example, for a given room, a temperature gradient is determined based on temperature sensor data gathered by a sensor device (500) and a vent (200). Because the sensor device (500) is installed into an electrical power outlet at a height of about 18 inches above the floor and the vent (200) is installed in a duct opening about 84 inches from the floor, a vertical temperature gradient for the room can be determined based on a linear model. Based upon the gradient and a temperature measurement from the sensor device (500), the system can determine the temperature of the room at 54 inches from the floor (at the average human chest height) without the need to place a temperature sensor at that particular height. In a similar way, temperature measurements made by a system thermostat (e.g., located about 54 inches from the floor) can be used by the system to determine temperature gradients. The preceding height measurements are merely illustrative, as vents can be installed directly in the floor (i.e., at a height of zero), in the ceiling (e.g., at a height of 96-144 inches), at any position within the wall (e.g., 0-144 inches), and independent from a wall, as in an exposed duct work installation. In embodiments that use sensor readings from vent (200), readings can be taken when the system detects that the HVAC system's air handler has been off for a specified period of time, so as to avoid the influence of heated or cooled air on the sensor measurement. Similarly, the system can monitor the sensor readings taken by the vent (200) over time after the air handler has stopped in order to detect when the sensed environmental variable has stabilized.

The vertical heights of the sensor device (500) and vent (200) can be provided by the user of the system during installation or can be estimated based on the pressure altitude determined by pressure sensor readings taken by the various devices. In some embodiments, data collected by the sensor information aggregator is used to infer a relative vertical position for one or more sensors embedded in sensor devices (500) and/or vents (200). For example, if a majority of the pressure altitude measurements for a collection of sensor devices (500) are approximately the same, the system can infer that those sensor devices (500) are installed in electrical power outlets at a standard installation height. The same determinations can be made for installations of vents (500) in walls, ceilings, or floor locations.

Also as set forth above, certain embodiments of single sensor platforms, such as sensor device (500), have more than one sensor of a given type, and data collected from the multiple sensors on the device are used to determine an environmental variable gradient in the room in which the device is disposed. For example, certain embodiments of sensor device (500) have two temperature sensors—a first (520) located on the face that is closest to the wall when the device is installed in an electrical power outlet (shown generally in FIGS. 20 and 21) and a second located on the opposite face (shown generally in FIG. 20 at 515.) In situations where a temperature differential is detected between the first and second temperature sensors on the device, the system can infer that a boundary layer exists along the wall. Such differentials, and resulting boundary layers, can occur on the inside of exterior walls of a building. The differential is driven, at least in part, by external sources or sinks of heat, such as outside air temperature and potential solar loading. The result is that the air near the wall is heated or cooled by the wall surface and natural convective forces create an airflow.

Figure 33:
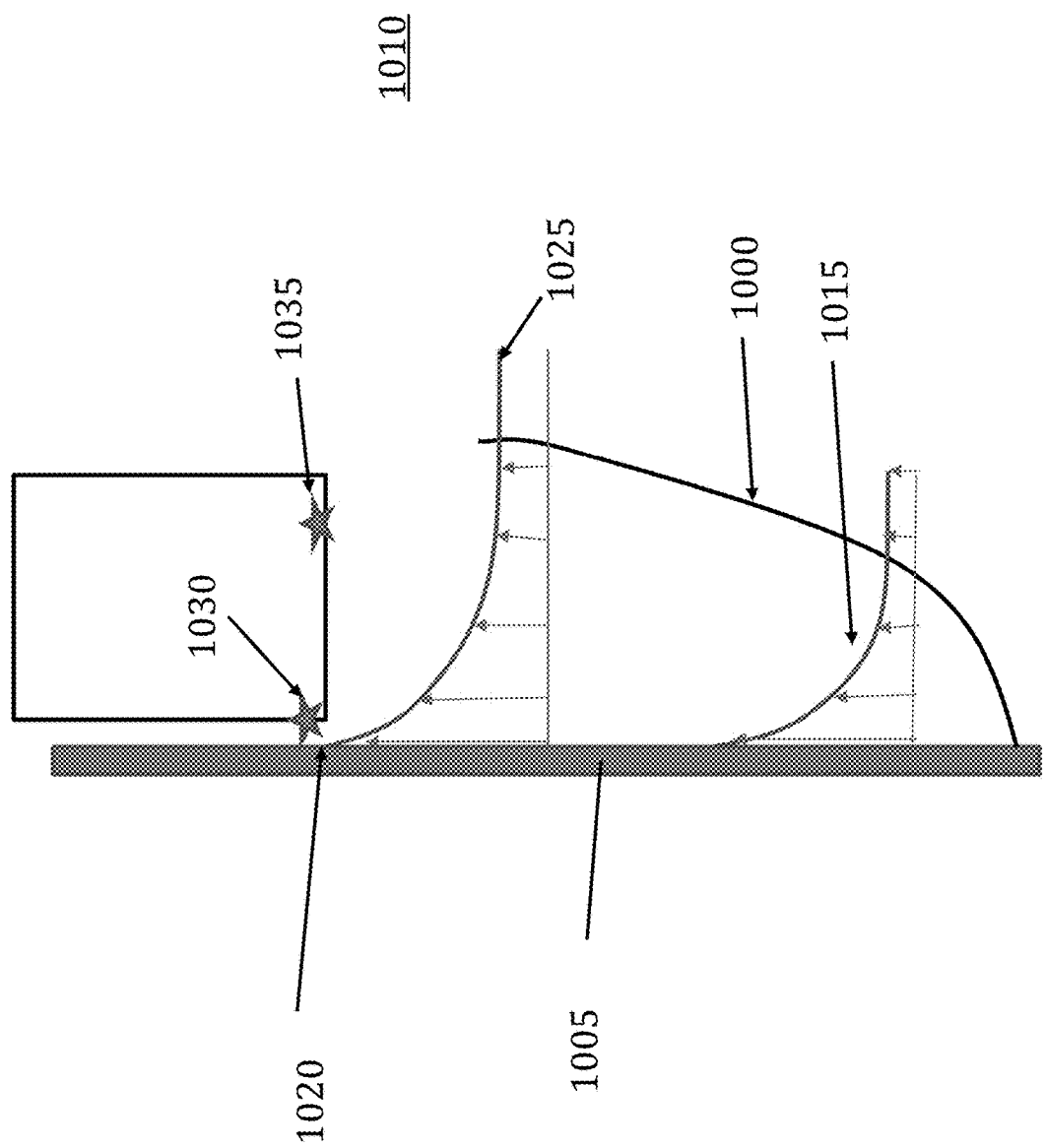
FIG. 33 illustrates a boundary layer formed by a temperature differential between a wall and a room interior.

FIG. 33 illustrates a boundary layer 1000 formed by a temperature differential between a wall 1005 and a room interior 1010 when the wall 1005 is subjected to an external heat source. The convective airflow effects the shape of the temperature gradient 1015 that starts at the wall 1005 and moves to the center of the room interior 1010. By measuring a temperature at a point near the wall at the base of the boundary layer 1020, and a temperature at another point further out in the boundary layer 1025, the system can extrapolate to infer a temperature at the center of the room. As mentioned above, pressure measurements can be used to estimate a sensor device's height from the floor, which, in turn, enables the system to estimate boundary layer thickness at the sensor location. In general, it is expected that the boundary layer will be well developed in the vast majority of cases, rendering the effect of vertical location of the sensor device along the wall insubstantial.

Thus, to correct for the effect the boundary layer has on the temperature measurement for the room in which the device is disposed, the temperature differential is used, along with the known horizontal spacing between the first temperature sensor 1030 and the second temperature sensor 1035 (e.g., about one inch) to determine a horizontal temperature gradient present in the room. When determining a horizontal temperature gradient for a room, in some embodiments, an exponential function is used to predict the temperature of the room outside of the boundary layer effect. In other embodiments, the function is determined empirically. In still further embodiments, the temperature outside of the boundary layer is determined using known methods, such as those disclosed in J. Padet, *Transient Convective Heat Transfer* (J. Braz. Soc. Mech. Sci. & Eng. vol. 27 no. 1 Rio de Janeiro January/March 2005.) In some embodiments, the position of the sun in the sky at the location of the system installation is an additional input when determining the effect of the boundary layer upon the measurement of temperature within a room. In general, the boundary layer thickness increases with an increase in solar loading. Exterior rooms (e.g., rooms with at least one wall shared with the exterior of the building) are impacted more significantly by the position of the sun within the sky than interior rooms. For example, the temperature differential due to the boundary effect is more pronounced when the sun is relatively higher in the sky than at other times. Likewise, the relative position of the room in the entire building impacts the magnitude of the boundary layer effect—a room with an eastern exposure is relatively more impacted during the first half of the day, while a room with a western exposure is relatively more impacted during the second half of the day. This east-west positional impact is magnified in more southern latitudes as compared to more northern latitudes. The position of the sun is correlated with the time of day based upon the latitude of the system installation. The latitude of the installation can be obtained during installation, e.g., based on a zip code provided by the user or based on an IP address observed by the system during installation using known techniques.

Sensed environmental variable gradients can also be used by the system to infer the relative locations of the rooms of the building. The system can then make control decisions based on the gradients and/or relative locations. For example, should the system detect an increasing temperature gradient from a first set of rooms to a second set of rooms, the system can infer the first set of rooms are located lower in the building than the second set of rooms. Because heat rises, the system can take the information derived from the gradient into account when performing control actions. Thus, in certain implementations, when the system is in an active heating mode, the system will open vents present in lower rooms of the building relatively more than vents present in upper rooms of the building. Conversely, such an implementation would reverse the bias when an in active cooling mode. In the cooling mode, the system would open the vents in the upper rooms relatively more than the vents in the lower rooms. As mentioned above regarding the aggregator, a processor in any of the components of the system described herein can perform the determination of the gradient values based on the information supplied by the various sensors and system components.

Certain aspects of the techniques and systems disclosed herein may be implemented as a computer program product for use with a computer system or computerized electronic device. Such implementations may include a series of computer instructions, or logic, fixed either on a tangible medium, such as a computer readable medium (e.g., a diskette, CD-ROM, ROM, flash memory or other memory or fixed disk) or transmittable to a computer system or a device, via a modem or other interface device, such as a communications adapter connected to a network over a medium.

The medium may be either a tangible medium (e.g., optical or analog communications lines) or a medium implemented with wireless techniques (e.g., Wi-Fi, cellular, microwave, infrared or other transmission techniques). The series of computer instructions embodies at least part of the functionality described herein with respect to the system. Those skilled in the art should appreciate that such computer instructions can be written in a number of programming languages for use with many computer architectures or operating systems.

Furthermore, such instructions may be stored in any tangible memory device, such as semiconductor, magnetic, optical or other memory devices, and may be transmitted using any communications technology, such as optical, infrared, microwave, or other transmission technologies.

It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of both software (e.g., a computer program product) and hardware. Still other embodiments of the invention are implemented as entirely hardware, or entirely software (e.g., a computer program product).

Preferred embodiments of the invention are described above as having communications, routing, and processing functions located in various components of the system. For example, the sensor platform 201 can act as a repeater for other system components. However, these functions can be distributed in other components of the system and remain within the scope of the invention. Thus, for example, vents can communicate directly with a thermostat, a control interface, or any other system component. Likewise, the determination of operating parameters that is described as being performed by one particular component can be performed by another component.

The invention claimed is:

1. A system comprising:
   a sensor assembly comprising:
   a first face,
   a second face, the second face being on the opposite side of the sensor assembly relative to the first face, and the second face being spaced apart from the first face,
   a first sensor disposed adjacent to the first face, the first sensor configured to sense a first value of an environmental variable in proximity to the first face, and
   a second sensor disposed adjacent to the second face, the second sensor configured to sense a second value of the environmental variable in proximity to the second face;
   a processor and a memory readable by the processor, the memory comprising instructions that when executed cause the processor to:
   receive the first value of the environmental variable,
   receive the second value of the environmental variable, and
   estimate a third value of the environmental variable at a distance spaced apart from the second face based on the first and second values of the environmental variable; and
   a sensor communication system configured to transmit information, the information including at least one of the first, second, and third value of the environmental variable.

2. The system of claim 1, the sensor assembly including the processor and the memory.

3. The system of claim 2, the sensor assembly including the sensor communication system.

4. The system of claim 1, the sensor assembly further comprising:
   an electrical plug disposed on the first face of the sensor assembly; and
   an electrical outlet disposed on the second face of the sensor assembly,
   the sensor assembly being configured such that the first face is disposed adjacent to a wall surface when the electrical plug of the sensor assembly is coupled to an electrical outlet in the wall surface.

5. The system of claim 1, the memory further comprising instructions that when executed cause the processor to receive information about a time of day and cause the processor to further base the estimate of the third value of the environmental variable on the time of day.

6. The system of claim 1, the memory further comprising instructions that when executed cause the processor to further base the estimate of the third value of the environmental variable on a distance of separation between the first sensor and the second sensor.

7. The system of claim 1, wherein the first sensor and the second sensor are temperature sensors, and the environmental variable is temperature.

8. The system of claim 7, wherein the estimate of the third value of the environmental variable at the distance spaced apart from the second face estimates the temperature of a room in which the sensor assembly is disposed.

9. A method comprising:
   providing a sensor assembly comprising:
   a first face,
   a second face, the second face being on the opposite side of the sensor assembly relative to the first face, and the second face being spaced apart from the first face,
   a first sensor disposed adjacent to the first face, the first sensor configured to sense a first value of an environmental variable in proximity to the first face, and
   a second sensor disposed adjacent to the second face, the second sensor configured to sense a second value of the environmental variable in proximity to the second face;
   receiving the first value of the environmental variable at a processor;
   receiving the second value of the environmental variable at the processor;
   estimating, by the processor, a third value of the environmental variable at a distance spaced apart from the second face based on the first and second values of the environmental variable; and
   transmitting at least one of the first, second, and third value of the environmental variable.

10. The method of claim 9, further comprising receiving information about a time of day, and wherein the estimating, by the processor, of the third value of the environmental variable being further based on the time of day.

11. The method of claim 9, wherein the estimating, by the processor, of the third value of the environmental variable being further based on a distance of separation between the first sensor and the second sensor.

12. The method of claim 9, wherein the first sensor and the second sensor are temperature sensors, and the environmental variable is temperature.

13. The method of claim 9, wherein the estimate of the third value of the environmental variable at the distance spaced apart from the second face estimates the temperature of a room in which the sensor assembly is disposed.

14. The method of claim 9, wherein the sensor assembly includes the processor, and wherein the sensor assembly further comprises a transmitter configured to transmit the at least one of the first, second, and third values of the environmental variable.

15. The method of claim 14, wherein the transmitting of the at least one of the first, second, and third values of the environmental variable includes transmitting the third value.

16. The method of claim 9, the sensor assembly further comprising:
   an electrical plug disposed on the first face of the sensor assembly; and an electrical outlet disposed on the second face of the sensor assembly, the sensor assembly being configured such that the first face is disposed adjacent to a wall surface when the electrical plug of the sensor assembly is coupled to an electrical outlet in the wall surface.

\* \* \* \* \*